United States Patent
Piron et al.

(10) Patent No.: US 11,931,140 B2
(45) Date of Patent: Mar. 19, 2024

(54) SYSTEMS AND METHODS FOR NAVIGATION AND SIMULATION OF MINIMALLY INVASIVE THERAPY

(71) Applicant: SYNAPTIVE MEDICAL INC., Toronto (CA)

(72) Inventors: Cameron Piron, Toronto (CA); Michael Wood, Toronto (CA); Gal Sela, Toronto (CA); Joshua Richmond, Toronto (CA); Murugathas Yuwaraj, Toronto (CA); Monroe M. Thomas, Toronto (CA); Wes Hodges, Toronto (CA); Simon Alexander, Toronto (CA); David Gallop, Toronto (CA); Alex Panther, Toronto (CA); Nishanthan Shanmugaratnam, Toronto (CA); William Lau, Toronto (CA)

(73) Assignee: SYNAPTIVE MEDICAL INC.

( * ) Notice: Subject to any disclaimer, the term of this patent is extended or adjusted under 35 U.S.C. 154(b) by 0 days.

(21) Appl. No.: 17/819,653

(22) Filed: Aug. 15, 2022

(65) Prior Publication Data
US 2022/0386891 A1    Dec. 8, 2022

Related U.S. Application Data

(63) Continuation of application No. 16/449,265, filed on Jun. 21, 2019, now Pat. No. 11,412,951, which is a
(Continued)

(51) Int. Cl.
| | | |
|---|---|---|
| A61B 5/06 | (2006.01) | |
| A61B 5/00 | (2006.01) | |
| A61B 5/055 | (2006.01) | |
| A61B 5/145 | (2006.01) | |
| A61B 17/34 | (2006.01) | |
| A61B 34/10 | (2016.01) | |

(Continued)

(52) U.S. Cl.
CPC ............ *A61B 5/065* (2013.01); *A61B 5/0042* (2013.01); *A61B 5/0095* (2013.01); *A61B 5/055* (2013.01); *A61B 5/14539* (2013.01); *A61B 17/3421* (2013.01); *A61B 34/20* (2016.02); *A61B 90/90* (2016.02); *A61B 2034/107* (2016.02); *A61B 2034/2051* (2016.02); *A61B 2034/2053* (2016.02); *A61B 2034/2055* (2016.02); *A61B 2034/2063* (2016.02); *A61B 2090/103* (2016.02); *A61B 2090/365* (2016.02); *A61B 2090/3735* (2016.02); *A61B 2090/3762* (2016.02); *A61B 2090/3782* (2016.02); *A61B 2090/3983* (2016.02); *A61B 90/50* (2016.02); *A61B 2090/571* (2016.02); *A61B 2562/0247* (2013.01); *A61N 1/0534* (2013.01)

(58) Field of Classification Search
None
See application file for complete search history.

(56) References Cited

PUBLICATIONS

Piron et al., "Systems and Methods for Navigation and Simulation of Minimally Invasive Therapy", U.S. Appl. No. 16/449,265, filed Jun. 21, 2019, Notice of Allowance issued.

*Primary Examiner* — Jonathan Cwern

(57) ABSTRACT

Navigation and simulation systems and methods for minimally invasive therapy in which the navigation system imports a planning method using patient specific preoperative images. The navigation system uses intraoperative imaging during the medical procedure to update the preoperative images and provides images of tracked surgical tools along the surgical path prepared from the preoperative images.

20 Claims, 20 Drawing Sheets

Related U.S. Application Data continuation of application No. 14/655,814, filed as application No. PCT/CA2014/050270 on Mar. 14, 2014, now Pat. No. 10,433,763.

(60) Provisional application No. 61/924,993, filed on Jan. 8, 2014, provisional application No. 61/818,255, filed on May 1, 2013, provisional application No. 61/818,325, filed on May 1, 2013, provisional application No. 61/801,746, filed on Mar. 15, 2013, provisional application No. 61/801,155, filed on Mar. 15, 2013, provisional application No. 61/801,143, filed on Mar. 15, 2013.

(51) Int. Cl.
| | |
|---|---|
| *A61B 34/20* | (2016.01) |
| *A61B 90/00* | (2016.01) |
| *A61B 90/10* | (2016.01) |
| *A61B 90/50* | (2016.01) |
| *A61B 90/57* | (2016.01) |
| *A61B 90/90* | (2016.01) |
| *A61N 1/05* | (2006.01) |

SYSTEMS AND METHODS FOR NAVIGATION AND SIMULATION OF MINIMALLY INVASIVE THERAPY

CROSS-REFERENCE TO RELATED APPLICATIONS

This document is a continuation application and claims the benefit of, and priority to, U.S. patent application Ser. No. 16/449,265, entitled "SYSTEMS AND METHODS FOR NAVIGATION AND SIMULATION OF MINIMALLY INVASIVE THERAPY," filed on Jun. 21, 2019, U.S. patent application Ser. No. 14/655,814, entitled "SYSTEMS AND METHODS FOR NAVIGATION AND SIMULATION OF MINIMALLY INVASIVE THERAPY," filed on Jun. 26, 2015, International Application No. PCT/CA2014/050270, entitled "SYSTEMS AND METHODS FOR NAVIGATION AND SIMULATION OF MINIMALLY INVASIVE THERAPY," filed on Mar. 14, 2014, U.S. Provisional Application Ser. No. 61/800,155, entitled "PLANNING, NAVIGATION AND SIMULATION SYSTEMS AND METHODS FOR MINIMALLY INVASIVE THERAPY," filed on Mar. 15, 2013, U.S. Provisional Application Ser. No. 61/924,993, entitled "PLANNING, NAVIGATION AND SIMULATION SYSTEMS AND METHODS FOR MINIMALLY INVASIVE THERAPY," filed on Jan. 8, 2014, U.S. Provisional Application Ser. No. 61/801,746, entitled "INSERT IMAGING DEVICE," filed on Mar. 15, 2013, U.S. Provisional Application Ser. No. 61/818,255, entitled "INSERT IMAGING DEVICE," filed on May 1, 2013, U.S. Provisional Application Ser. No. 61/801,143, entitled "INSERTABLE MAGNETIC RESONANCE IMAGING COIL PROBE FOR MINIMALLY INVASIVE CORRIDOR-BASED PROCEDURES," filed on Mar. 15, 2013, and U.S. Provisional Application Ser. No. 61/818,325, entitled "INSERTABLE MAGNETIC RESONANCE IMAGING COIL PROBE FOR MINIMALLY INVASIVE CORRIDOR-BASED PROCEDURES," filed on May 1, 2013, all of which are hereby incorporated herein by reference in their entirety.

FIELD

The present disclosure relates to navigation systems and methods for minimally invasive therapy and image guided medical procedures.

BACKGROUND

Minimally invasive neurosurgical procedures require geometrically accurate, and patient-registered, imaging data to facilitate tissue differentiation and targeting. Thusfar, true integration of imaging (presurgical and intraoperative), surgical access, and resection devices has not been accomplished. Medical devices remain separate systems, and the surgeon is required to cognitively integrate the information.

Preoperative imaging data such as Magnetic Resonance Imaging (MRI), Computerized Tomography (CT) and Positron Emission Tomography (PET), is integrated into the surgical room statically through a viewing station, or dynamically through a navigation system. The navigation system registers devices to a patient, and a patient to the preoperative scans, allowing for instruments to be viewed on a monitor in the context of the preoperative information.

Intraoperative imaging systems primarily consist of microscopes, endoscopes, or external video scopes. These are optical instruments that acquire, record and display optical wavelength imaging (2D, or stereoscopic) that is typically acquired at an increased resolution compared to what can be seen with the surgeon's unassisted eye. This optical information is typically displayed on a screen for the surgeon to view as a video feed, while the navigated MRI/CT/PET data would be presented on a separate screen.

Some attempts have been made to offer a small window on the navigation screen to show the optical video, or likewise showing overlays from the navigation screen on the optical video. Accurate registration between the modalities, effective interface between the surgeon and the devices, and true integration of the devices has remained elusive.

Port-based surgery is a minimally invasive surgical technique where a port is introduced to access the surgical region of interest using surgical tools. Unlike other minimally invasive techniques, such as laparoscopic techniques, the port diameter is larger than tool diameter. Hence, the tissue region of interest is visible through the port. Accordingly, exposed tissue in a region of interest at a depth a few centimeters below the skin surface, and accessible through a narrow corridor in the port. Several problems generally preclude or impair the ability to perform port-based navigation in an intraoperative setting. For example, the position of the port axis relative to a typical tracking device (TD) is a free and uncontrolled parameter that prohibits the determination of access port orientation. Furthermore, the limited access available due to the required equipment for the procedure causes indirect access port tracking to be impractical and unfeasible. Also, the requirement for angulation of the access port to access many areas within the brain during a procedure makes navigation of the access port a difficult and challenging problem that has not yet been addressed.

Further, a recent paper by Stieglitz et al., "The Silent Loss of Neuronavigation Accuracy: A Systematic Retrospective Analysis of Factors Influencing the Mismatch of Frameless Stereotactic Systems in Cranial Neurosurgery," highlights the need for accurate navigation, wherein after patient registration, there is an ongoing loss of neuronavigation accuracy due to other mitigating factors related to the surgical procedure, i.e., draping, attachment of skin retractors, and duration of surgery. Surgeons should be aware of this silent loss of accuracy when using navigation systems. Thus, a need exists for a system and method to integrate and update preoperative and intraoperative plans into navigation systems for minimally invasive surgical procedures.

SUMMARY

Disclosed herein is a navigation method and system used to execute a surgical plan during brain medical procedures. These procedures may include port-based surgery using a port with an introducer, deep brain stimulation or brain biopsy using needles. The navigation system is configured to utilize a plan based on a multi-segment path trajectory previously prepared based on preoperative anatomical information of the patient's brain. This plan is imported into the navigation software module. Prior to the procedure commencing, the brain is registered with its preoperative anatomical information. Once the craniotomy has been performed, the navigation method and system display an overlay image of the brain and the multi-point path trajectory. In addition, it provides a guidance mechanism to assist the surgeon in aligning the surgical tool (port, biopsy needle, catheter etc.) coaxially along the first path trajectory segment. Using port-based surgery as an example, once the port is aligned with the first path trajectory segment the surgeon begins the cannulation procedure and moves the port introducer along the first segment while the system and method assists the surgeon in remaining consistently coaxial with the path segment and displays to the surgeon the distance of the introducer along the first segment until the end of the segment is reached. The surgeon then changes direction to follow the second trajectory segment. The process is repeated until the target location is reached.

The method and system provide the surgeon with positional information of the patient's anatomy of interest throughout the course of the medical procedure using video overlay, e.g., allowing the surgeon to see the brain through the drapes and therefore know his/her orientation relative to the patient). This allows the surgeon to more accurately identify potential locations of anatomical structures of the brain intraoperatively as opposed to performing the procedure without a rendered overlay of the anatomical part. The system and method allow the surgeon to confirm that they have the correct anatomical data of the patient more effectively than presently used systems. This is because in the present method and system the imaged anatomy is rendered onto the real-time imaging of the patient anatomy allowing the surgeon to compare the rendered image of the anatomical part with the real anatomical part, for example, comparing the sulci locations during a port procedure.

The method and system provide for tracking of multiple tools during surgery relative to the brain, so the surgeon is not "flying blind." For example, the system can track the port as well as any tools being used in conjunction with the port, such as a resection tool in case of tumor resection, whereas presently used systems track only a pointer tool.

The navigation method and system provide a setup for the surgery to the surgical team based on a predetermined plan, e.g., setup of the head clamp, position of patient, tracking device, etc., to prevent readjustments of such elements during surgery. The navigation method and system are configured to adaptively update a section of a larger preoperative MRI image using a localized intraoperative MRI image (given that the brain is internally accessible from within the skull). The navigation method and system provide positionally accurate maps (images) correlating intraoperative information acquired during surgery, such as hyperspectral and Raman signatures to locations where the information was acquired. For example, these signatures may be represented by spatially correlated color maps.

The above-described method and system, while primarily described for port-based brain surgery, is not limited to port-based brain surgery and is applicable to any surgery that utilizes a navigation system. Thus, a port may not be used; and the anatomical part may be any part of the anatomy. This system can be utilized with any animal other than and including humans.

A further understanding of the functional and advantageous aspects of the present disclosure can be realized by reference to the following detailed description and drawings.

BRIEF DESCRIPTION OF THE DRAWINGS

The embodiments disclosed herein will be more fully understood from the following detailed description thereof taken in connection with the accompanying drawings, which form a part of this application, and in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

The systems and methods described herein are useful in the field neurosurgery, including oncological care, neurodegenerative disease, stroke, brain trauma, and orthopedic surgery; however, these concepts are extendable to other conditions or fields of medicine. The surgical process is applicable to surgical procedures for brain, spine, knee and any other region of the body that will benefit from the use of an access port or small orifice to access the interior of the human body.

Various apparatuses or processes will be described below to provide examples of embodiments of the navigation method and system disclosed herein. No embodiment described below limits any claimed embodiment and any claimed embodiments may cover processes or apparatuses that differ from those described below. The claimed embodiments are not limited to apparatuses or processes having all the features of any one apparatus or process described below or to features common to multiple or all of the apparatuses or processes described below. Possible is that an apparatus or process described below is not an embodiment of any claim.

Furthermore, numerous specific details are set forth in order to provide a thorough understanding of the embodiments described herein. However, the embodiments described herein may be practiced without these specific details. In other instances, well-known methods, procedures and components have not been described in detail so as not to obscure the embodiments described herein.

Figure 1:
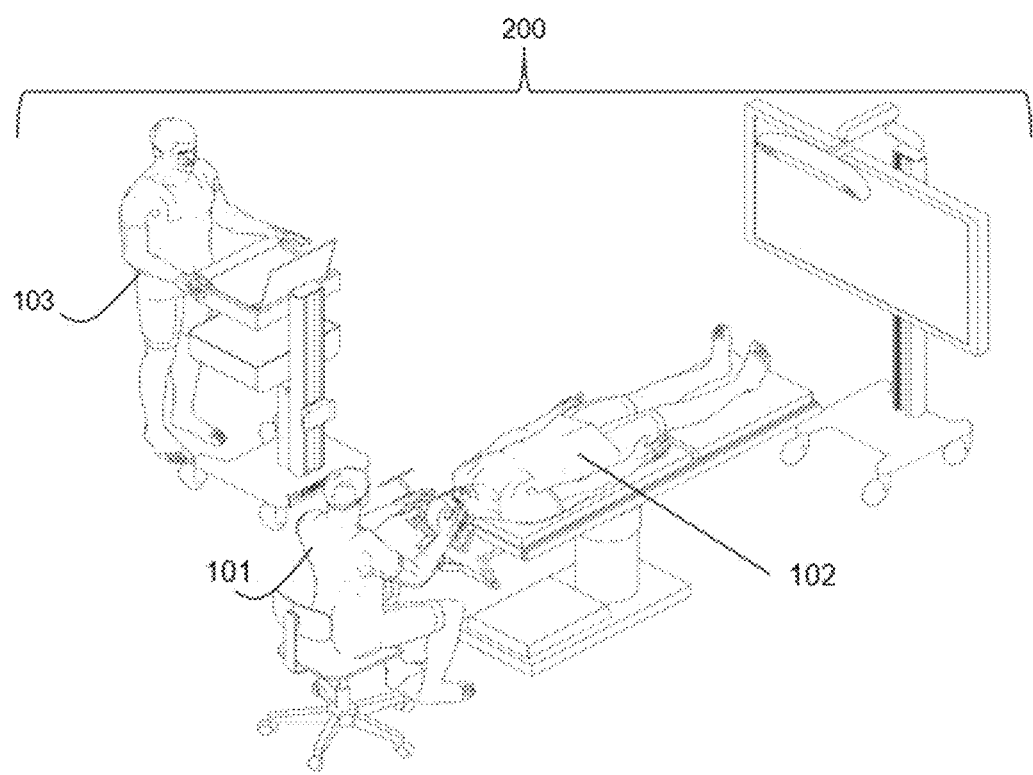
FIG. 1 is a diagram illustrating an exemplary navigation system to support minimally invasive access port-based surgery, in accordance with an embodiment of the present disclosure.

Referring to FIG. 1, this diagram illustrates, in a perspective view, an exemplary navigation system to support minimally invasive access port-based surgery, in accordance with an embodiment of the present disclosure. A surgeon 101 conducts a minimally invasive port-based surgery on a patient 102 in an operating room (OR) environment. A navigation system 200 comprising an equipment tower, tracking system, displays and tracked instruments assist the surgeon 101 during his procedure. An operator 103 is also present to operate, control, and provide assistance for the navigation system 200.

Figure 2:
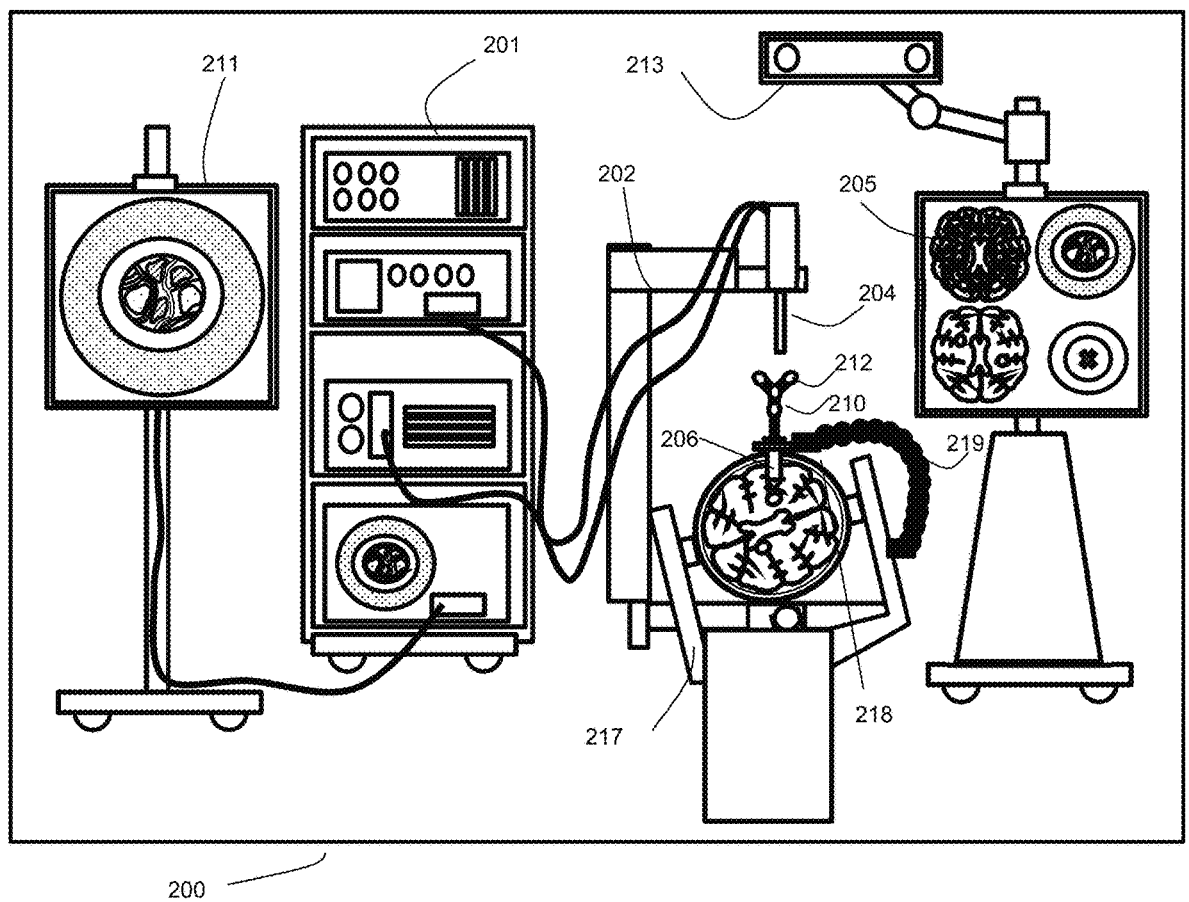
FIG. 2 is a block diagram illustrating system components of a navigation system, in accordance with an embodiment of the present disclosure.

Referring to FIG. 2, this block diagram illustrates system components of an exemplary navigation system, in accordance with an embodiment of the present disclosure. Navigation system 200 includes a monitor 211 for displaying a video image, an equipment tower 201, a mechanical arm 202, which supports an optical scope 204. Equipment tower 201 is mounted on a frame, e.g., a rack or cart, and may contain a computer, planning software, navigation software, a power supply and software to manage the automated arm and tracked instruments. The exemplary embodiment envisions the equipment tower 201 as a single tower configuration with dual displays 211, 205, however, other configurations may also exist, e.g., dual tower, single display, etc. Furthermore, equipment tower 201 may also be configured with a UPS (universal power supply) to provide for emergency power, in addition to a regular AC adapter power supply.

Still referring to FIG. 2, the patient's brain is held in place by a head holder 217 and inserted into the head is an access port 206 and introducer 210. The introducer 210 may also be considered a pointing tool. The introducer 210 may be tracked using a tracking system 213, which provides position information for the navigation system 200. Tracking system 213 may be a 3D optical tracking stereo camera similar to one made by Northern Digital Imaging (NDI). Location data of the mechanical arm 202 and port 206 may be determined by the tracking system 213 by detection of fiducial markers 212 placed on these tools. A secondary display 205 may provide output of the tracking system 213. The output may be shown in axial, sagittal and coronal views (or views oriented relative to the tracked instrument such as perpendicular to tool tip, in-plane of tool shaft, etc.) as part of a multi-view display.

Still referring to FIG. 2, minimally invasive brain surgery using access ports is a recently conceived method of performing surgery on brain tumors. In order to introduce an access port into the brain, an introducer 210 with an atraumatic tip may be positioned within the access port and employed to position the access portion within the head. As noted above, the introducer 210 may include fiducial markers 212 for tracking. The fiducial markers 212 may be reflective spheres in the case of optical tracking systems or pick-up coils in the case of electromagnetic tracking systems. The fiducial markers 212 are detected by the tracking system 213 and their respective positions are inferred by the tracking software.

Still referring to FIG. 2, once inserted into the brain, the introducer 210 may be removed to allow for access to the tissue through the central opening of the access port. However, once introducer 210 is removed, the access port can no longer be tracked. Accordingly, the access port may be indirectly tracked by additional pointing tools configured for identification by the navigation system 200.

Still referring to FIG. 2, a guide clamp 218 for holding the access port 206 may be provided. Guide clamp 218 can optionally engage and disengage with access port 206 without needing to remove the access port from the patient. In some embodiments, the access port can slide up and down within the clamp while in the closed position. A locking mechanism may be attached to or integrated with the guide clamp, and can optionally be actuated with one hand, as described further below.

Still referring to FIG. 2, a small articulated arm 219 may be provided with an attachment point to hold guide clamp 218. Articulated arm 219 may have up to six degrees of freedom to position guide clamp 218. Articulated arm 219 may be attached or attachable to a point based on patient head holder 217, or another suitable patient support, to ensure when locked in place, guide clamp 218 cannot move relative to the patient's head. The interface between guide clamp 218 and articulated arm 219 may be flexible, or optionally locked into place. Flexibility is desired so the access port can be moved into various positions within the brain, but still rotate about a fixed point.

Still referring to FIG. 2, an example of such a linkage that can achieve this function is a slender bar or rod. When the access port 206 is moved to various positions, the bar or rod will oppose such a bend, and move the access port 206 back to the centered position. Furthermore, an optional collar may be attached to the linkage between the articulated arm, and the access port guide, such that when engaged, the linkage becomes rigid. Currently, no such mechanisms exist to enable positioning an access port in such a manner.

Still referring to FIG. 2, in a surgical operating room (or theatre), setup of a navigation system may be complicated; there may be many pieces of equipment associated with the surgical procedure, as well as the navigation system. Further, setup time increases as more equipment is added. One possible solution is an extension of the exemplary navigation system 200 where two additional wide-field cameras are implemented with video overlay information. One wide-field camera may be mounted on optical scope 204, and a second wide-field camera may be mounted on the navigation system 213. Alternatively, in the case of an optical tracking system a video image can possibly be extracted directly from the camera within the tracking system 213. Video overlay information can then be inserted into the images, where the video overlay may provide the following information: "illustrate physical space and confirm tracking system registration alignment," "illustrate range of motion of a robot used to hold the external scope," and "guide head positioning and patient positioning."

Figure 3A:
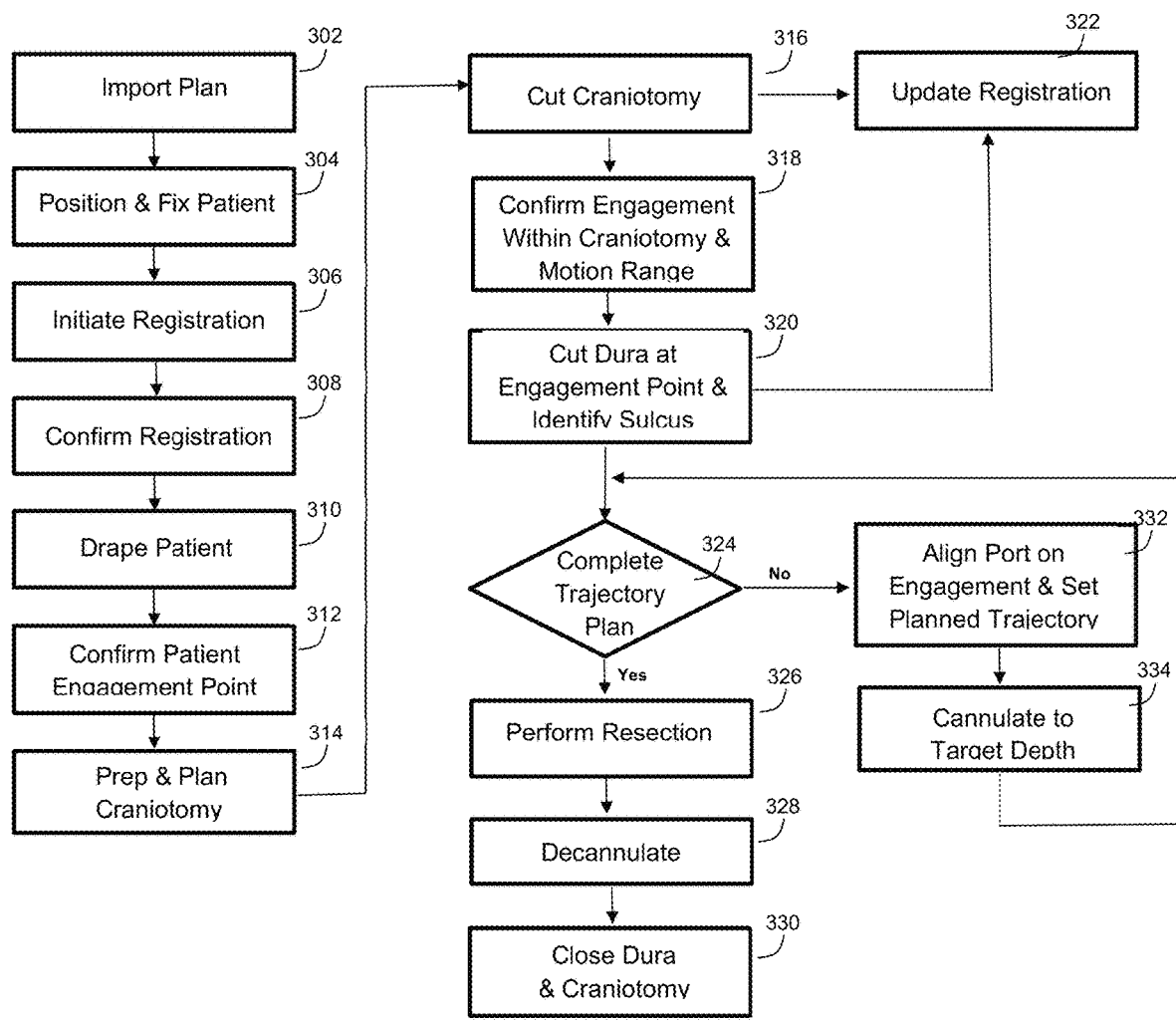
FIG. 3A is a flow chart illustrating the processing steps involved in a port-based surgical procedure using a navigation system, in accordance with an embodiment of the present disclosure.

Referring to FIG. 3A, this flow chart illustrates the processing steps involved in a port-based surgical procedure using a navigation system, in accordance with an embodiment of the present disclosure. The first step involves importing the port-based surgical plan (step 302). A detailed description of a process to create and select a surgical plan is outlined in the disclosure "PLANNING, NAVIGATION AND SIMULATION SYSTEMS AND METHODS FOR MINIMALLY INVASIVE THERAPY" United States Patent Publication US20160070436 based on U.S. patent application Ser. No. 14/769,668, which claims the priority benefit of U.S. Provisional Patent Application Ser. Nos. 61/800,155 and 61/924,993, and wherein for the purposes of this present United States patent application, the Detailed Description and Figures of United States Patent Application Publication No. 2016/0070436 are incorporated herein by reference.

Still referring to FIG. 3A, an exemplary plan, as outlined above, may compose of preoperative 3D imaging data, e.g., MRI, CT, ultrasound (US), etc., and overlaying on it, received inputs, e.g., sulci entry points, target locations, surgical outcome criteria, additional 3D image data information, and displaying one or more trajectory paths based on the calculated score for a projected surgical path. 3D images comprise three spatial dimensions. In another embodiment, the three spatial dimensions comprise two spatial dimensions (as in the case of MR "slice" images as acquired by conventional MR equipment) and time as the third dimension. A further embodiment may include three spatial dimensions and time as the fourth dimension of the data set. Some imaging modalities and estimation methods, such as diffusion tensor imaging data, may contain more than four dimensions of information at each spatial location. The aforementioned surgical plan may be one example. Other surgical plans and/or methods may also be envisioned and may form the planning input into the present guidance and navigation system.

Figure 9:
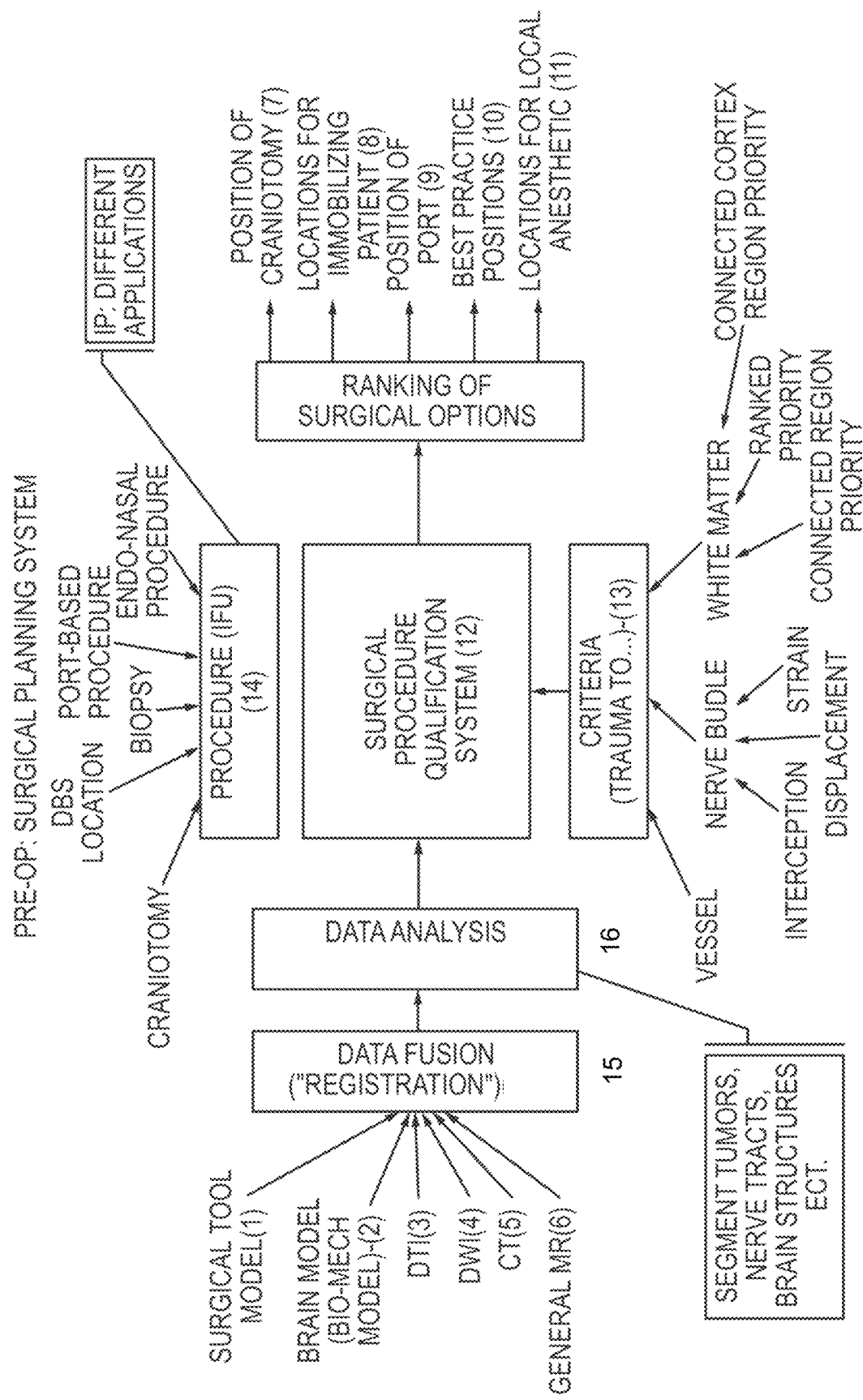
FIG. 9 is a block diagram is a diagram illustrating system components and inputs for planning and scoring surgical paths as disclosed herein, in accordance with an embodiment of the present disclosure.
Figure 10:
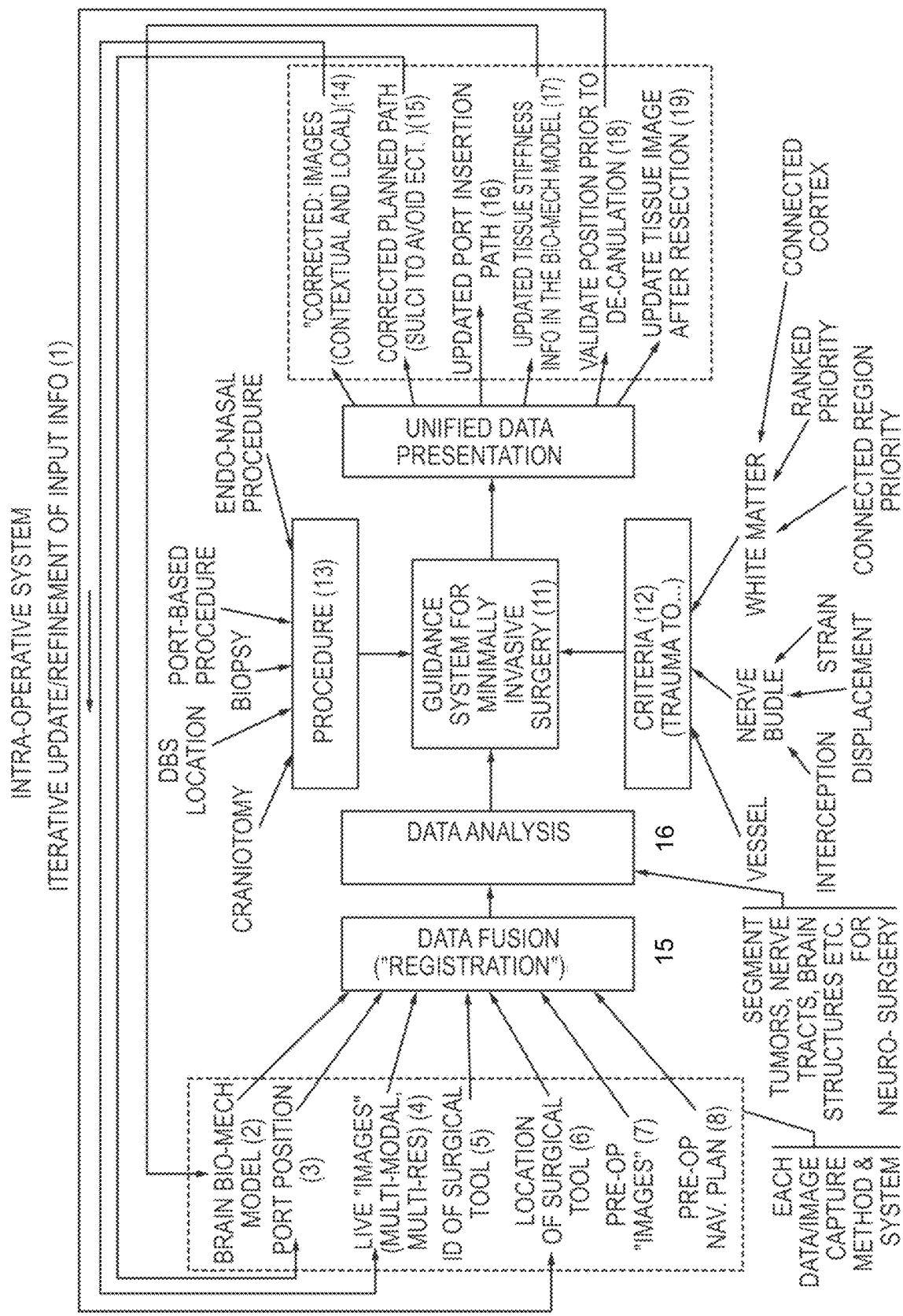
FIG. 10 is a block diagram is a diagram illustrating system components and inputs for navigation along the surgical paths produced by an exemplary planning system, as shown in FIG. 9, in accordance with an embodiment of the present disclosure.

Referring to FIG. 9, this block diagram illustrates system components and inputs for planning and scoring surgical paths as disclosed herein as disclosed in United States Patent Publication 2016/0070436 as above noted, in accordance with an embodiment of the present disclosure. FIG. 10 is a block diagram showing system components and inputs for navigation along the surgical paths produced by an exemplary planning system of FIG. 9.

Referring to FIG. 10, this block diagram illustrates an intraoperative system having system components and inputs for navigation along the surgical paths produced by an exemplary planning system, as shown in FIG. 9, in accordance with an embodiment of the present disclosure. The intraoperative multi-modal surgical planning and navigation system and method is used as a surgical planning and navigation tool in the preoperative and intraoperative stages. The data input(s) of the surgical planning steps and surgical procedures, as described in relation to FIG. 9, are used as input(s) to the intraoperative navigation stage.

Still referring to FIG. 10, the navigation system of provides a user, such as a surgeon, with a unified means of navigating through a surgical region by utilizing preoperative data input(s) and updated intraoperative data input(s). The processor(s) of system and methods are programmed with instructions/algorithms 11 to analyze preoperative data input(s) and intraoperative data input(s) to update surgical plans during the course of surgery. For example, if intraoperative input(s) in the form of newly acquired images identified a previously unknown nerve bundle or fiber track, these input(s) can, if desired, be used to update the surgical plan during surgery to avoid contacting the nerve bundle. The intraoperative input(s) may include a variety input(s) including local data gathered using a variety of sensor(s).

Still referring to FIG. 10, in some embodiments, the system and methods of FIG. 10 may provide continuously updated intraoperative input(s) in the context of a specific surgical procedure by means of intraoperative imaging sensor(s) to validate tissue position, update tissue imaging after tumor resection and update surgical device position during surgery.

Still referring to FIG. 10, the systems and methods may provide for reformatting of the image, for example, to warn of possible puncture of critical structures with the surgical tools during surgery, or collision with the surgical tool during surgery. In addition, the embodiments disclosed herein may provide imaging and input updates for any shifts that might occur due to needle deflection, tissue deflection or patient movement as well as algorithmic approaches to correct for known imaging distortions. The magnitude of these combined errors is clinically significant and may regularly exceed 2 cm. Some of the most significant are MRI based distortions such gradient non-linearity, susceptibility shifts, eddy current artifacts which may exceed 1 cm on standard MRI scanners (1.5 T and 3.0 T systems).

Still referring to FIG. 10, a variety of intraoperative imaging techniques can be implemented to generate intraoperative input(s) including anatomy specific MRI devices, surface array MRI scans, endonasal MRI devices, anatomy specific US scans, endonasal US scans, anatomy specific CT or PET scans, port-based or probe-based photo-acoustic imaging, as well as optical imaging done with remote scanning, or probe based scanning.

Referring back to FIG. 3A, once the plan has been imported into the navigation system (step 302), the patient is affixed into position using a head or body holding mechanism. The head position is also confirmed with the patient plan using the navigation software (step 304).

Figure 4A:
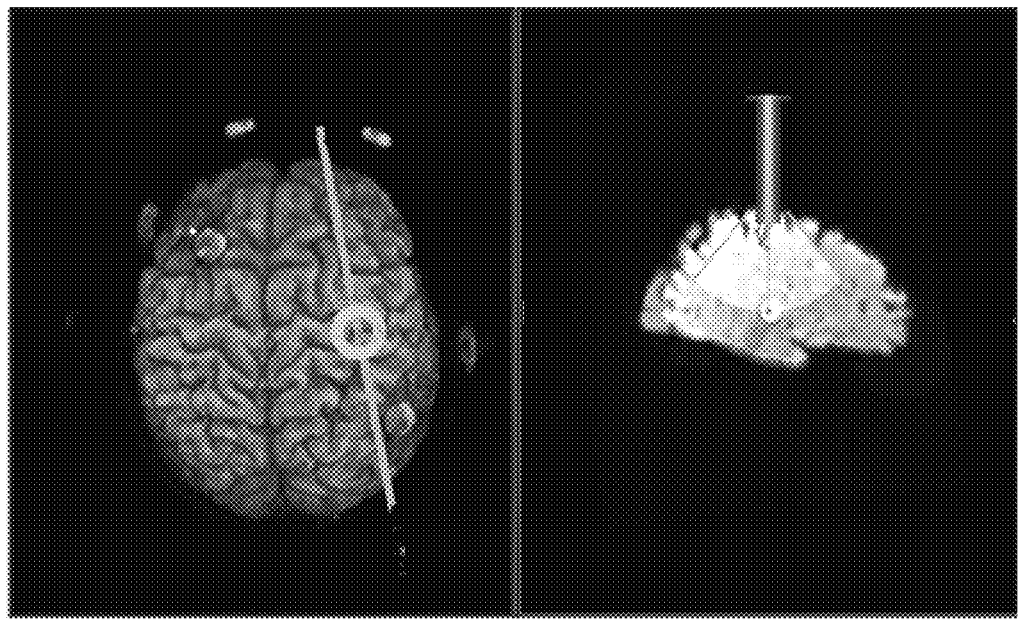
FIG. 4A is a diagram illustrating an example embodiment of the navigation system software illustrating the Patient Positioning step, in accordance with an embodiment of the present disclosure.

Referring to FIG. 4A, this diagram illustrates an example embodiment of the navigation system software executing the patient positioning step 304, in accordance with an embodiment of the present disclosure. In this embodiment, the plan is reviewed; and the patient positioning is confirmed to be consistent with craniotomy needs. Furthermore, a procedure trajectory may be selected from a list of planned trajectories produced in the planning procedure.

Referring back to FIG. 3A, the next step is to initiate registration of the patient (step 306). The phrase "registration" or "image registration" refers to the process of transforming different sets of data into one coordinate system. Registration of the patient to a base reference frame may occur in many ways. A few methods or registration techniques may comprise: identifying features (natural or engineered) on the MR and CT images and point to those same features in the live scene using a pointer tool that is tracked by the tracking system; tracing a line on the curved profile of the patient's face or forehead with a pointer tool that is tracked by the tracking system. Match this curved profile to the 3D MR or CT volume; applying a tool of known geometry to the face (This tool has the active or passive targets tracked by the tracking system.); and using a surface acquisition tool based on structured light. The extracted surface is then matched to the 3D MR or CT volume using standard techniques.

Still referring back to FIG. 3A, numerous registration techniques are available and one or more of them may be used in the present application. Non-limiting examples include intensity-based methods which compare intensity patterns in images via correlation metrics, while feature-based methods find correspondence between image features such as points, lines, and contours. Image registration algorithms may also be classified according to the transformation models they use to relate the target image space to the reference image space. Another classification can be made between single-modality and multi-modality methods. Single-modality methods typically register images in the same modality acquired by the same scanner/sensor type, for example, a series of MR images can be co-registered, while multi-modality registration methods are used to register images acquired by different scanner/sensor types, for example in MRI and PET.

Still referring back to FIG. 3A, in the present disclosure, multi-modality registration methods are used in medical imaging of the head/brain as images of a subject are frequently obtained from different scanners. Examples include registration of brain CT/MRI images or PET/CT images for tumor localization, registration of contrast-enhanced CT images against non-contrast-enhanced CT images, and registration of ultrasound and CT.

Figure 3B:
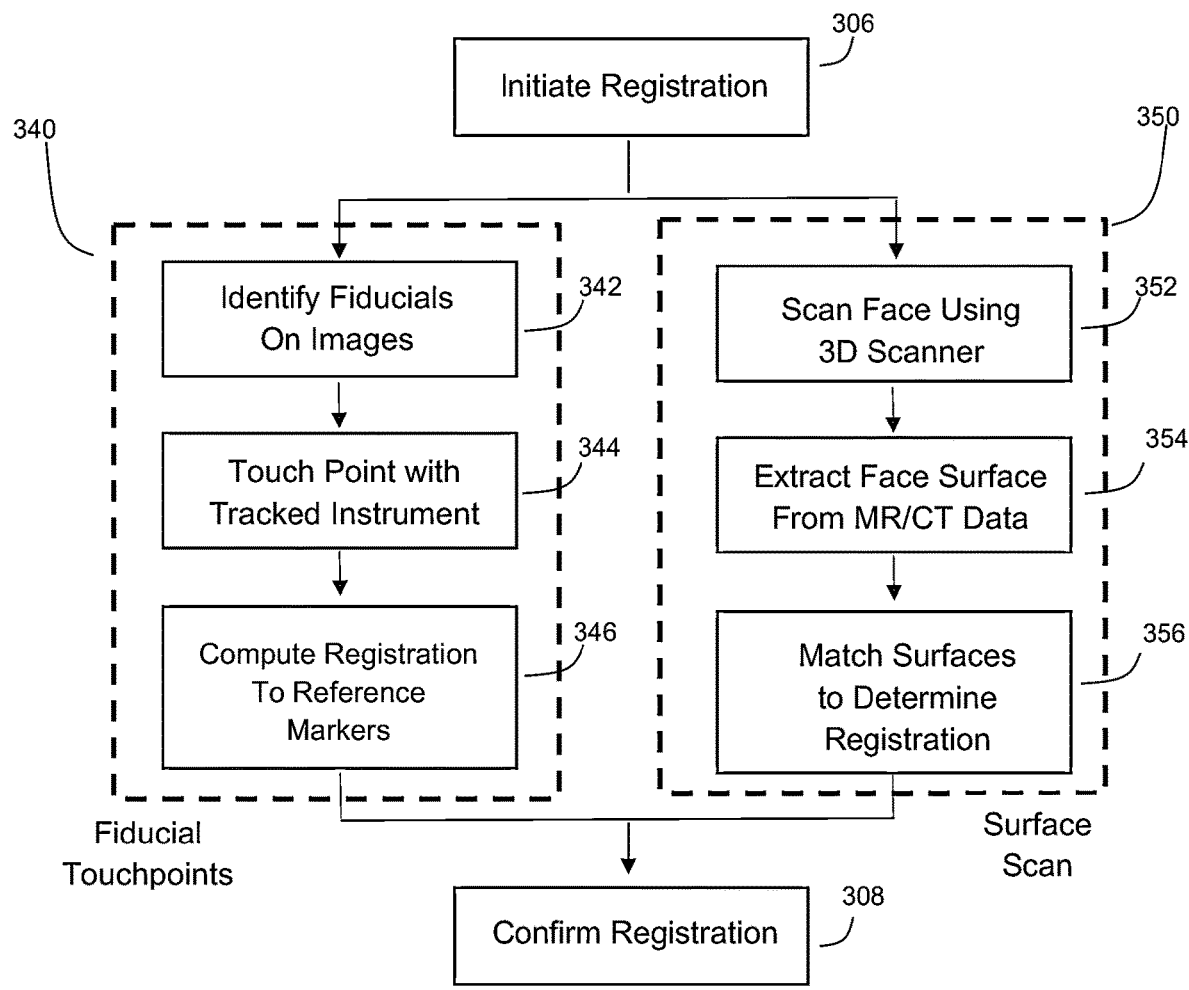
FIG. 3B is a flow chart illustrating the processing steps involved in registering a patient for a port-based surgical procedure, as shown in FIG. 3A, in accordance with an embodiment of the present disclosure.

Referring to FIG. 3B, this flow chart illustrates the further processing steps involved in registration as shown in FIG. 3A, in accordance with an embodiment of the present disclosure. In this exemplary embodiment, registration can be completed using fiducial touch points 340 captured by a pointing tool as described further in FIGS. 6A to 6D. If fiducial touchpoints 340 are contemplated, the process involves first identifying fiducial markers on images (step 342), then touching the fiducial touchpoints 340 with a tracked instrument 344. Next, the navigation system computes the registration to reference markers (step 346).

Still referring to FIG. 3B, registration can also be completed by conducting a surface scan procedure 350. The first step involves scanning the face using a 3D scanner (step 352). The next step is to extract the face surface from MR/CT data (step 354). Finally, surfaces are matched to determine registration data points. Upon completion of either the fiducial touchpoints 340 or surface scan 350 procedures, the data extracted is computed and used to confirm registration (step 308).

Figure 4B:
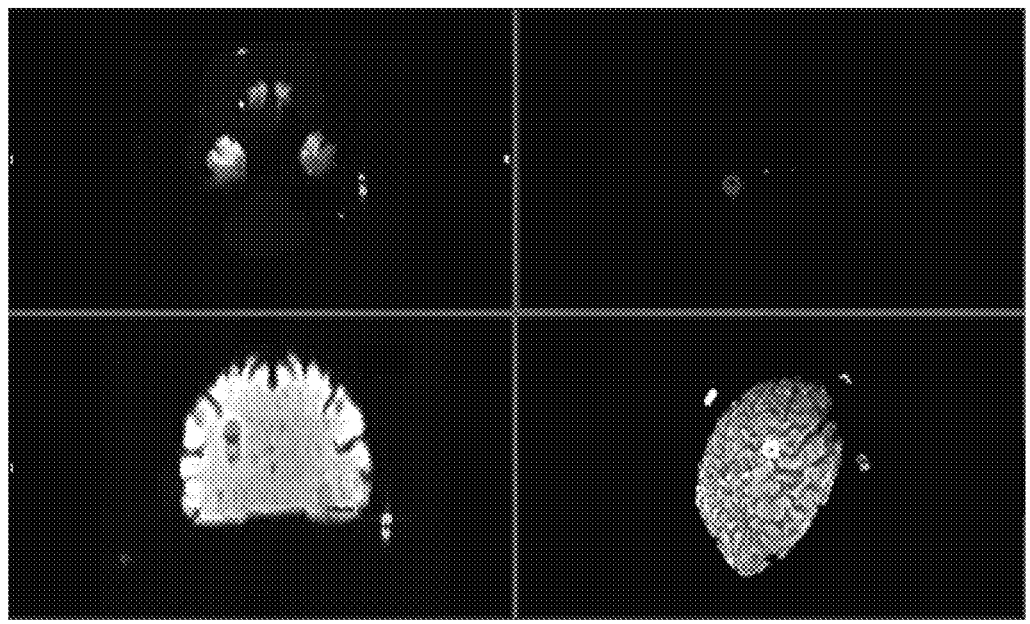
FIG. 4B is a diagram illustrating an example embodiment of the navigation system software illustrating the Registration step, in accordance with an embodiment of the present disclosure.

Referring to FIG. 4B, this screenshot illustrates the navigation system software performing the registration step using fiducial touchpoints, in accordance with an embodiment of the present disclosure. In a further embodiment, recovery of loss of registration may also be provided. A detailed description of a process to create and select a surgical plan is outlined in U.S. Patent Application Publication No. 2016/0000515, entitled "SYSTEM AND METHOD FOR DYNAMIC VALIDATION AND CORRECTION OF REGISTRATION, AND RECOVERY OF LOST REFERENCE, FOR SURGICAL NAVIGATION," based on U.S. patent application Ser. No. 14/775,759, which claims the priority benefit of U.S. Provisional Patent Application Ser. No. 61/799,735, and U.S. Patent Application Publication No. 2016/0000515, all of which are hereby incorporated herein by reference om their entirety.

Still referring to FIG. 4B, as disclosed therein, during a navigation procedure a handheld instrument is tracked using a tracking system, and a representation of the instrument's position and orientation may be provided and displayed as an overlay on a previously acquired or current image, such as a three-dimensional scan, of a patient's anatomy obtained with an imaging device or system, such as ultrasound, CT or MRI. To achieve this, a registration is needed between the coordinate frame of a tracking system, the physical location of the patient in space, and the coordinate frame of the corresponding image of the patient. This registration is typically obtained relative to a tracked reference marker, which is placed in a fixed position relative to the patient anatomy of interest and thus can be used as a fixed reference for the anatomy. Generally, this can be accomplished by attaching the reference to a patient immobilization frame (such as a clamp for skull fixation in neurosurgery), which itself is rigidly attached to the patient. However, the reference may be held to the frame, for example, through an arm, which can be bumped and accidentally moved, which creates a loss of registration.

Still referring to FIG. 4B, additionally, since the reference marker must be positioned so that it is visible by the navigation hardware (typically requiring line-of-sight for optical tracking, or otherwise within the observation or communication field of the tracking system), this tends to position the reference such that it is in the open thus more susceptible to accidental interaction and loss of registration. In situations of lost registration, a surgical procedure tends to be stopped while a new registration is computed, although this may not always be possible if, for example, the registration fiducial points or patient skin surface are no longer accessible due to the progression of the surgical procedure, and thus creating a need for a full re-registration or, in some cases even disabling navigation for the remainder of the procedure.

Still referring to FIG. 4B, once registration is confirmed (step 308), the patient is draped (step 310). Typically draping involves covering the patient and surrounding areas with a sterile barrier to create and maintain a sterile field during the surgical procedure. The purpose of draping is to eliminate the passage of microorganisms, e.g., bacteria, between non-sterile and sterile areas. Upon completion of draping (step 310), the next steps are to confirm patient engagement points (step 312) and then prep and plan craniotomy (step 314).

Figure 4C:
FIG. 4C is a diagram illustrating an example embodiment of the navigation system software illustrating the craniotomy step, in accordance with an embodiment of the present disclosure.

Referring to FIG. 4C, this diagram illustrates an example embodiment of the navigation system software performing the craniotomy preparation and planning step (step 314), in accordance with an embodiment of the present disclosure.

Upon completion of the craniotomy preparation and planning step (step 312), the next step is to perform the craniotomy (step 314) where a bone flap is temporarily removed from the skull to access the brain (step 316). Registration data can be updated with the navigation system at this point (step 322), such as by adding additional registration correspondence points within the craniotomy, e.g., the location of a visible blood vessel. The next step is to confirm the engagement within craniotomy and the motion range (step 318). Once this data is confirmed, the procedure advances to the next step of cutting the dura at the engagement points and identifying the sulcus (step 320).

Figure 4D:
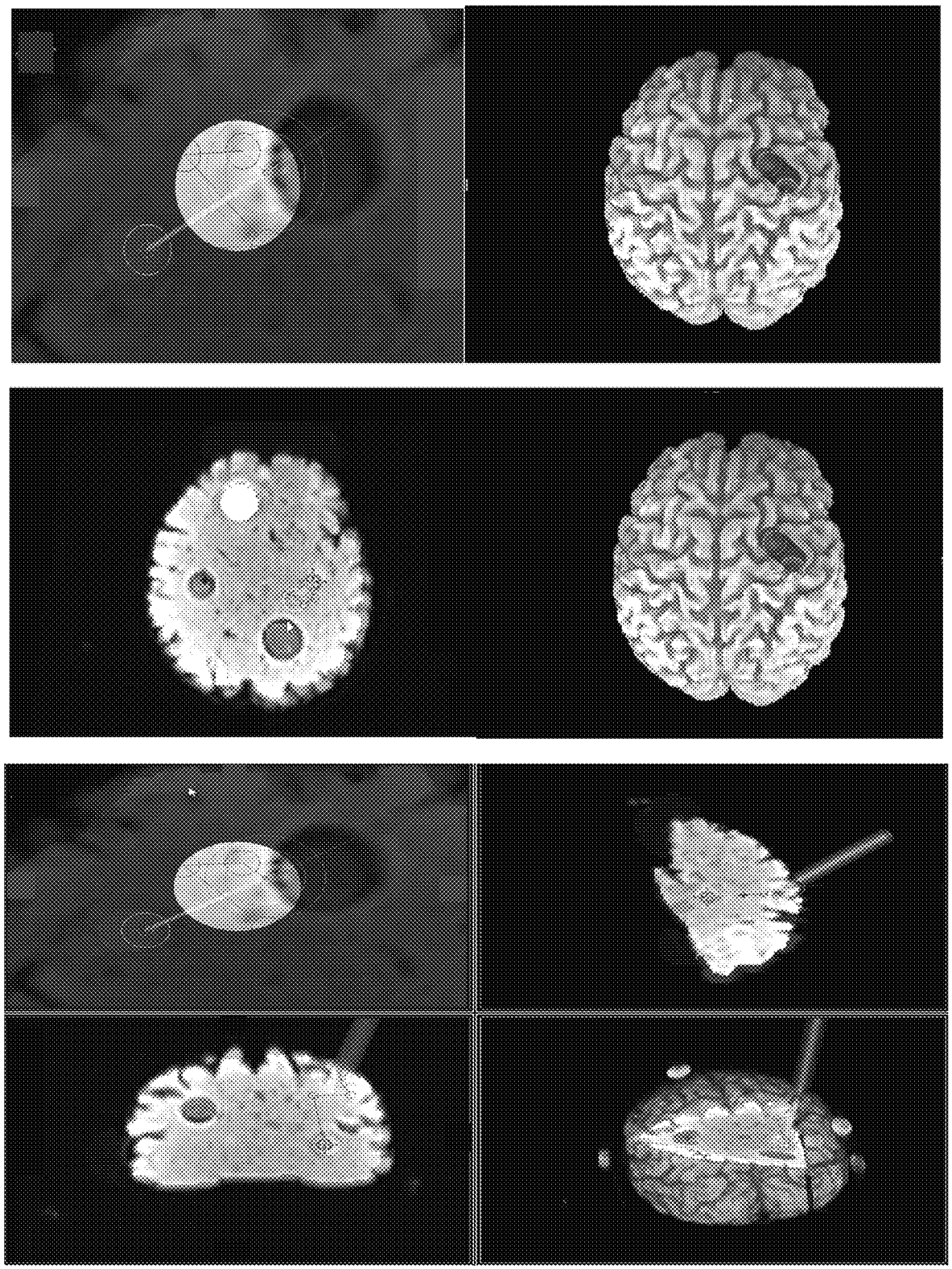
FIG. 4D is a diagram illustrating example embodiments of the navigation system software illustrating the Engagement step, in accordance with an embodiment of the present disclosure.

Referring to FIG. 4D, this diagram illustrates the navigation system software illustrating the engagement steps (steps 318 and 320), in accordance with some embodiments of the present disclosure. Registration data can be updated with the navigation system at this point (step 322), such as by adding additional registration correspondence points near the engagement point, e.g., a bifurcation of the entry sulcus. In an embodiment, by focusing the wide field camera's gaze on the surgical area of interest, this registration update can be manipulated to ensure the best match for that region, while ignoring any non-uniform tissue deformation affecting areas outside of the surgical field (of interest).

Still referring to FIG. 4D, additionally, by matching overlay representations of tissue with an actual view of the tissue of interest, the particular tissue representation can be matched to the video image, and thus tending to ensure registration of the tissue of interest. For example, the embodiment can (either manually or automatically): match video of post craniotomy brain, e.g., brain exposed, with imaged sulcal map; and/or match video position of exposed vessels with image segmentation of vessels; and/or match video position of lesion or tumor with image segmentation of tumor; and/or match video image from endoscopy up nasal cavity with bone rendering of bone surface on nasal cavity for endonasal alignment. The above method is described in detail in a co-pending U.S. patent application Ser. No. 14/775,759. In other embodiments, multiple cameras can be used and overlaid with tracked instrument(s) views, and, thus, allowing multiple views of the data and overlays to be presented at the same time, which can tend to provide even greater confidence in a registration, or correction in more dimensions/views.

Referring to FIG. 4D, thereafter, the cannulation process is initiated (step 324). Cannulation involves inserting a port into the brain, typically along a sulci path as identified in step 320, along a trajectory plan, in accordance with an embodiment of the present disclosure. Cannulation is an iterative process that involves repeating the steps of aligning the port on engagement and setting the planned trajectory (step 332) and then cannulating to the target depth (step 334) until the complete trajectory plan is executed (step 324).

Figure 4E:
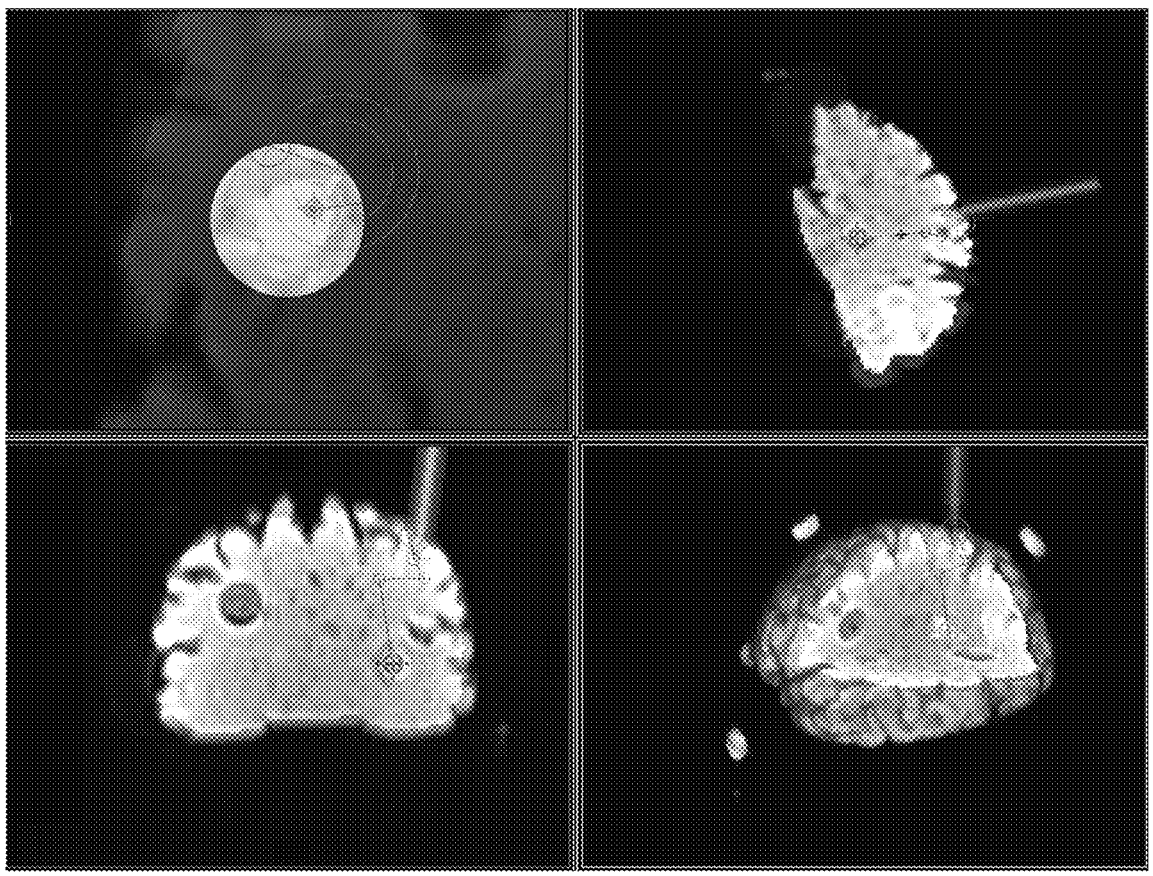
FIG. 4E is a diagram illustrating an example embodiment of the navigation system software illustrating the Cannulation step, in accordance with an embodiment of the present disclosure.

Referring to FIG. 4E, this diagram illustrates a navigation system software performing the cannulation steps, in accordance with an embodiment of the present disclosure. The cannulation process (step 324) may also support multi-point trajectories where a target, e.g., a tumor, may be accessed by pushing to intermediate points, then adjusting the angle to get to the next point in planned trajectory. This process allows trajectories to skirt around tissue that one may want to preserve, or ensure, staying within a sulcus to avoid damaging neighboring tissue. Navigating multi-point trajectories may be accomplished by physically reorienting a straight port at different points along a (planned) path, or by having a flexible port that has a number of manipulable bends that can be set along the path. The surgeon then decannulates (step 326) by removing the port and any tracking instruments from the brain. The surgeon then performs resection (step 328) to remove part of the brain and/or tumor of interest. Finally, the surgeon closes the dura and completes the craniotomy (step 330).

Still referring to FIG. 4E, in a further embodiment, the navigation system relates to fiber structures of the brain (nerves, ligaments, etc.) that can be re-imaged and registered so that it can be intraoperatively addressed using different modalities. In a further embodiment, quantitative registration may also be addressed. Quantitative registration refers to the ability to measure an absolute quantitative metric and use that to register between imaging modalities. These quantitative metrics may include T1, T2, cell density, tissue density, tissue anisotropy, tissue stiffness, fluid flow per volume or area, electrical conductivity, pH, and pressure.

Figure 5:
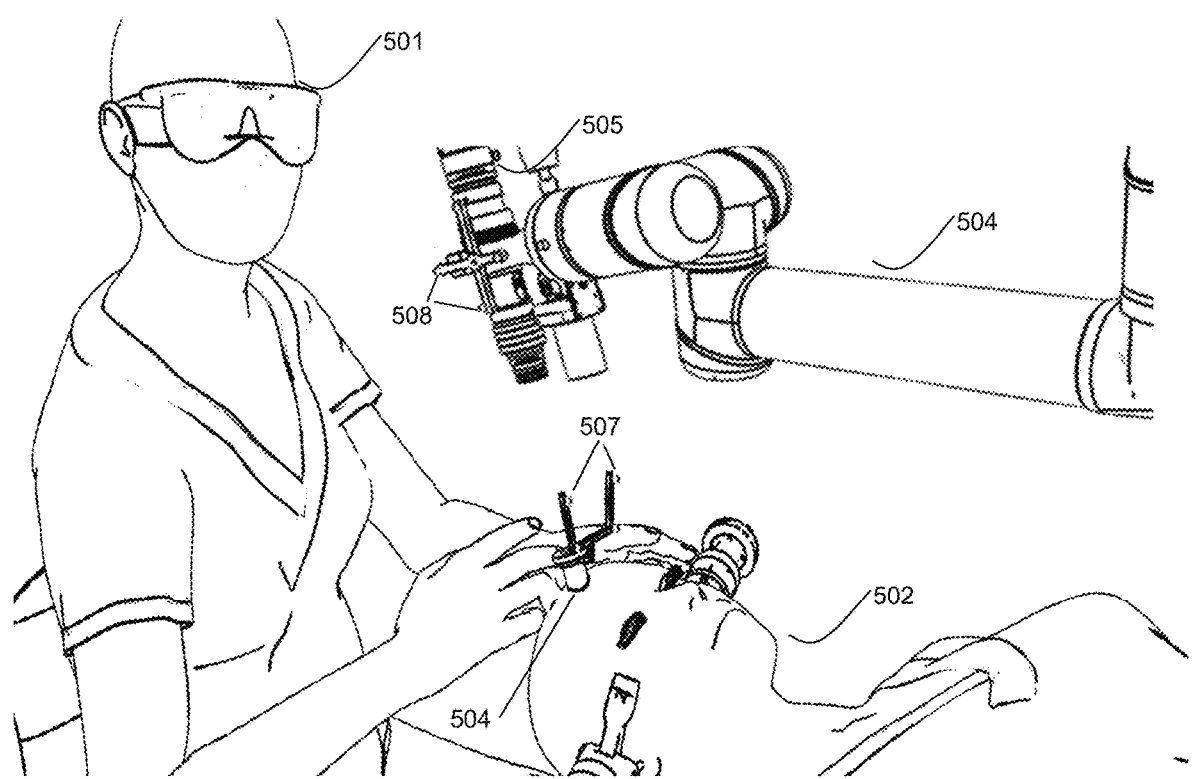
FIG. 5 is a diagram illustrating tracking of tools in a port-based surgical procedure, in accordance with an embodiment of the present disclosure.

Referring to FIG. 5, this diagram illustrates performance of a port-based surgical procedure. The surgeon 501 resects a tumor out of the brain of a patient 502 through port 504, in accordance with an embodiment of the present disclosure. External scope 505 is attached to mechanical arm 504 and is used to view down port 504 at a sufficient magnification to allow for enhanced visibility down port 504. The output of external scope 505 view is depicted on a visual display. Active or passive fiduciary spherical markers (507 and 508) may be placed on port 504 and/or external scope 505 to determine the location of these tools by the tracking system. The spheres are seen by the tracking system to give identifiable points for tracking. A tracked instrument is typically defined as a grouping of spheres, e.g., defining a rigid body to the tracking system. This is used to determine the position and pose in 3D of a tracked instrument. Typically, a minimum of three spheres are placed on a tracked tool to define the instrument. In the figures of this disclosure, four spheres are used to track each tool.

Still referring to FIG. 5, in a preferred embodiment, the navigation system may utilize reflectosphere markers in combination with an optical tracking system to determine spatial positioning of the surgical instruments within the operating field. The spatial position of automated mechanical arm(s) used during surgery may be also tracked in a similar manner. Differentiation of the types of tools and targets and their corresponding virtual geometrically accurate volumes could be determined by the specific orientation of the reflectospheres relative to one another giving each virtual object an individual identity within the navigation system. The individual identifiers would relay information to the system as to the size and virtual shape of the tool within the system. The identifier could also provide information such as the tool's central point, the tool's central axis, etc. The virtual tool may also be determinable from a database of tools provided to the navigation system. The marker positions could be tracked relative to an object in the operating room such as the patient.

Still referring to FIG. 5, other types of markers that could be used would be RF, EM, LED (pulsed and unpulsed), glass spheres, reflective stickers, unique structures and patterns, where the RF and EM would have specific signatures for the specific tools they would be attached to. The reflective stickers, structures and patterns, glass spheres, LEDs could all be detected using optical detectors, while RF and EM could be picked up using antennas. Advantages to using EM and RF tags would include removal of the line-of-sight condition during the operation, where using optical system removes the additional noise from electrical emission and detection systems.

Still referring to FIG. 5, in a further embodiment, printed or 3-D design markers could be used for detection by an auxiliary camera and/or external scope. The printed markers could also be used as a calibration pattern to provide distance information (3D) to the optical detector. These identification markers may include designs such as concentric circles with different ring spacing, and/or different types of bar codes. Furthermore, in addition to using markers, the contours of known objects, e.g., side of the port, top ring of the port, shaft of pointer tool, etc., could be made recognizable by the optical imaging devices through the tracking system.

Figure 6A:
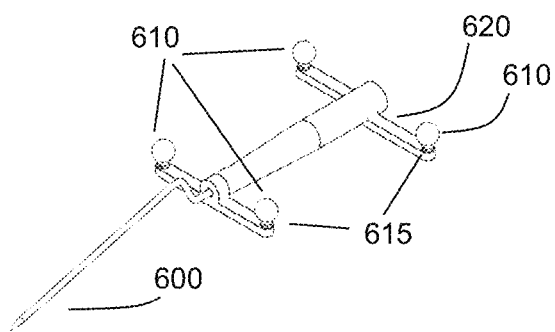
FIGS. 6A to 6D are diagrams illustrating exemplary pointing tools with tracking markers, in accordance with an embodiment of the present disclosure.
Figure 6B:
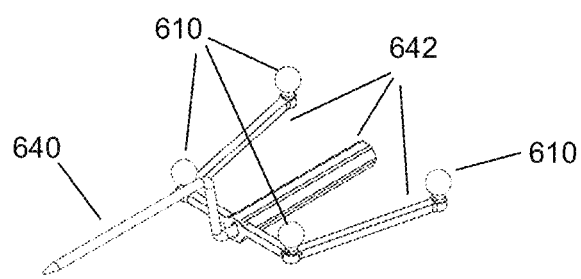
Figure 6C:
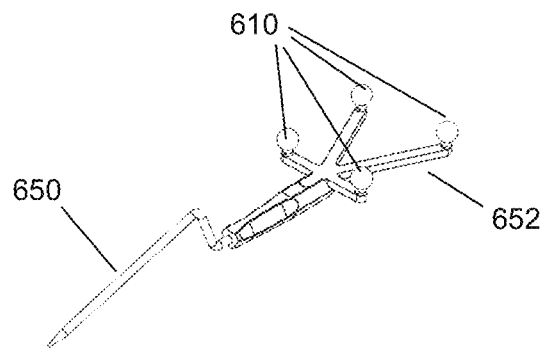
Figure 6D:
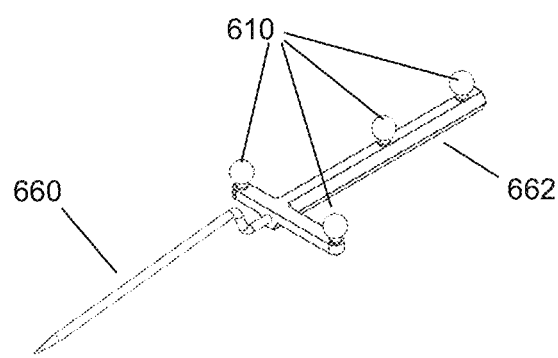

Referring to FIGS. 6A to 6D, together, these diagrams illustrate perspective views of exemplary pointing tools with fiducial or tracking markers, in accordance with some embodiment of the present disclosure. Referring to FIG. 6A, tracking marker 610 is placed on connector beam 615 attached to arm 620 of pointing tool 600. A minimum of three (3) tracking markers 610, and preferably four (4) markers, are placed on the tool 600 to track it with a tracking system. FIGS. 6B to 6D illustrate other embodiments of pointing tools with tracking markers 610 placed in various orientations and positions. For example, tracking tool 640 of FIG. 6B is connected to a supporting arm structure 642 to which four tracking markers 610 are rigidly attached. Tracking tool 650 of FIG. 6C is connected to a supporting arm structure 652, having a different configuration to arm support structure 652 of FIG. 6B, to which four tracking markers 610 are rigidly attached. Tracking tool 660 of FIG. 6D is connected to a supporting arm structure 662 different configurations from structures 652, 642 and 620, to which four tracking markers 610 are rigidly attached.

Figure 6E:
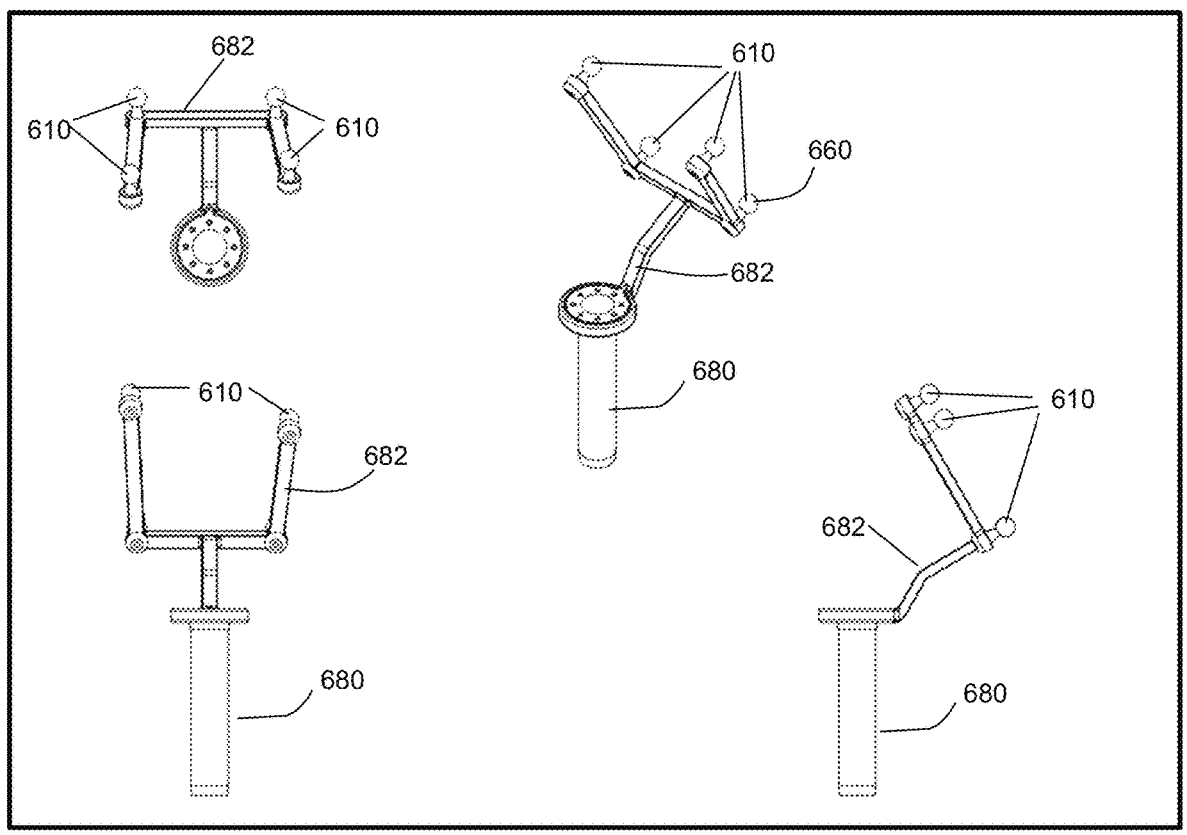
FIG. 6E is a diagram illustrating an exemplary port with tracking markers, in accordance with an embodiment of the present disclosure.

Referring to FIG. 6E, this diagram illustrates various perspectives of an embodiment of an access port 680 where fiducial or tracking markers 610 are placed on an extended arm 682 that is firmly attached to the access port 680, in accordance with an embodiment of the present disclosure. This arrangement enables clear visibility of the markers to the tracking device. Further, the extended arm 682 ensures that the markers 610 do not interfere with surgical tools that may be inserted through the access port 680. The non-uniform structure of the support arm for the fiducial markers 610 enables the tracking software to discern both the position and orientation of the access port.

Figure 7:
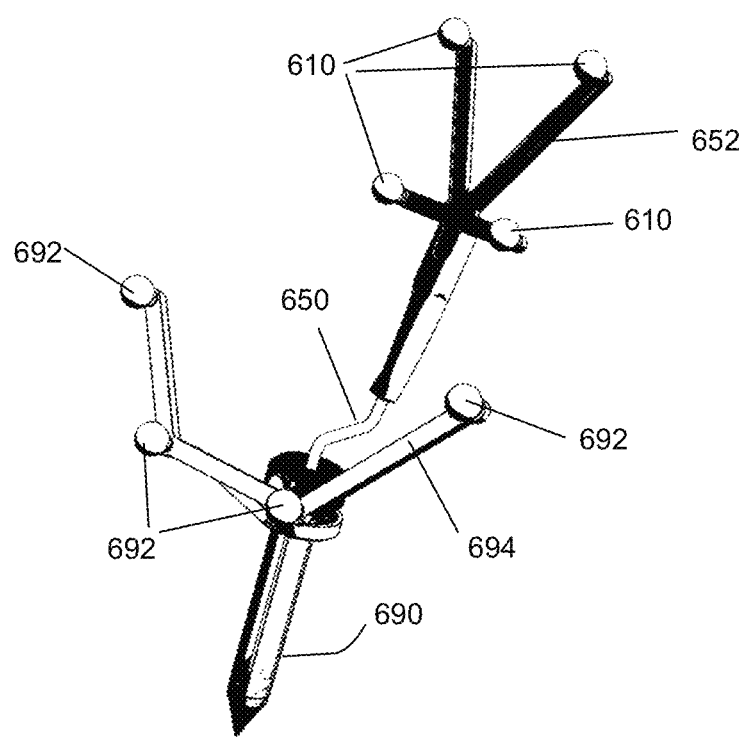
FIG. 7 is a diagram illustrating an exemplary port and pointing tool with tracking markers, in accordance with an embodiment of the present disclosure.

Referring to FIG. 7, this diagram illustrates an exemplary embodiment of pointing tool 650, with associated support arm structure 652, as shown in FIG. 6C, with associated fiducial markers 610, inserted into a port 690 which has its own fiducial markers 692 on associate arm support structure 694, in accordance with an embodiment of the present disclosure. Both the pointing tool and port are equipped with arms configured with tracking markers. These tools with tracking markers can then be tracked separately by the navigation system and differentiated as unique objects on the display.

Figure 8:
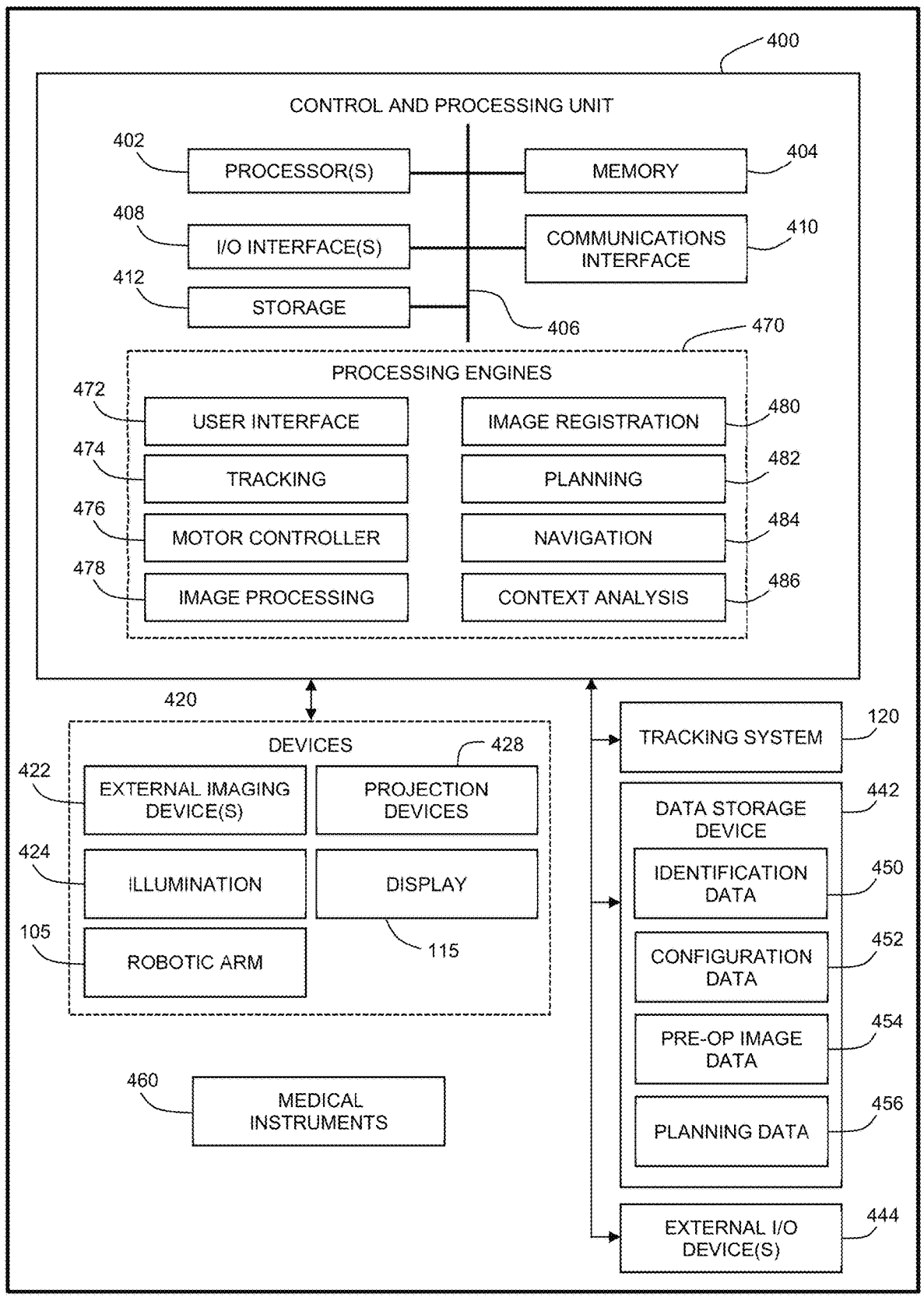
FIG. 8 is a diagram illustrating an example system inclusive of all of its independent parts and the components with which these independent parts would interact, in accordance with an embodiment of the present disclosure.

Referring to FIG. 8, this block diagram illustrates an example system configuration, in accordance with an embodiment of the present disclosure. The example system includes a control and processing unit 400 and a number of external components, shown below. In one embodiment, the control and processing unit 400 comprises one or more processors 402, a memory 404, a system bus 406, one or more input/output interfaces 408, and a communications interface 410, and storage device 412. Control and processing unit 400 is interfaced with other external devices, such as tracking system 120, data storage 442, and external user input and output devices 444, which may include, for example, one or more of a display, keyboard, mouse, foot pedal, microphone, and speaker.

Still referring to FIG. 8, the data storage 442 comprises any suitable data storage device, such as a local or remote computing device, e.g., a computer, hard drive, digital media device, or server) having a database stored thereon. The data storage device 442 includes identification data 450 for identifying one or more medical instruments 460 and configuration data 452 that associates customized configuration parameters with one or more medical instruments 460. Data storage device 442 may also include preoperative image data 454 and/or medical procedure planning data 456. Although data storage device 442 is shown as a single device, in other embodiments, the data storage device 442 comprises multiple storage devices. In a further embodiment, various 3D volumes, at different resolutions, may each be captured with a unique timestamp and/or quality metric. This data structure provides an ability to move through contrast, scale and time during the procedure and may also be stored in data storage device 442.

Still referring to FIG. 8, medical instruments 460 are identifiable by control and processing unit 400. Medical instruments 460 may be connected to, and controlled by, control and processing unit 400, or may be operated or otherwise employed independent of control and processing unit 400. Tracking system 120 may be employed to track one or more of medical instruments and spatially register the one or more tracked medical instruments to an intraoperative reference frame.

Still referring to FIG. 8, the control and processing unit 400 is also interfaced with a number of configurable devices and may intraoperatively reconfigure one or more of such devices based on configuration parameters obtained from configuration data 452. Examples of devices 420 comprise one or more external imaging device 422, one or more illumination devices 424, robotic arm 105, one or more projection devices 428, and one or more displays 115.

Still referring to FIG. 8, embodiments of the disclosure can be implemented via processor(s) 402 and/or memory 404. For example, the functionalities described herein can be partially implemented via hardware logic in processor 402 and partially using the instructions stored in memory 404, as one or more processing engines 470. Example processing engines include, but are not limited to, user interface engine 472, tracking engine 474, motor controller 476, image processing engine 478, image registration engine 480, procedure planning engine 482, navigation engine 484, and context analysis module 486.

Still referring to FIG. 8, the system is not intended to be limited to the components shown in the Figures. One or more components of the control and processing unit 400 may be provided as an external component or device. In one alternative embodiment, navigation module 484 may be provided as an external navigation system that is integrated with control and processing unit 400. Some embodiments may be implemented using processor 402 without additional instructions stored in memory 404. Some embodiments may be implemented using the instructions stored in memory 404 for execution by one or more general purpose microprocessors. Thus, the disclosure is not limited to a specific configuration of hardware and/or software.

Still referring to FIG. 8, while some embodiments can be implemented in fully functioning computers and computer systems, various embodiments are capable of being distributed as a computing product in a variety of forms and are capable of being applied regardless of the particular type of machine or computer readable media used to actually effect the distribution.

Still referring to FIG. 8, at least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, nonvolatile memory, cache or a remote storage device.

Still referring to FIG. 8, a computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

Still referring to FIG. 8, the preceding example embodiments have described systems and methods in which a device is intraoperatively configured based on the identification of a medical instrument. In other example embodiments, one or more devices may be automatically controlled and/or configured by determining one or more context measures associated with a medical procedure. A "context measure", as used herein, refers to an identifier, data element, parameter or other form of information that pertains to the current state of a medical procedure. In one example, a context measure may describe, identify, or be associated with, the current phase or step of the medical procedure.

Still referring to FIG. 8, in another example, a context measure may identify the medical procedure, or the type of medical procedure, which is being performed. In another example, a context measure may identify the presence of a tissue type during a medical procedure. In another example, a context measure may identify the presence of one or more fluids, such as biological fluids or non-biological fluids, e.g., wash fluids, during the medical procedure, and may further identify the type of fluid. Each of these examples relates to the image-based identification of information pertaining to the context of the medical procedure.

Still referring to FIG. 8, examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media, e.g., compact discs (CDs), digital versatile disks (DVDs), etc., among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Still referring to FIG. 8, furthermore, at least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer usable instructions may also be in various forms, including compiled and non-compiled code.

Still referring to FIG. 8, a purpose of the navigation system is to provide tools to the neurosurgeon that will lead to the most informed, least damaging neurosurgical operations. In addition to port-based removal of brain tumors and intracranial hemorrhages (ICH), the navigation system can also be applied to brain biopsy, functional/deep-brain stimulation, catheter/shunt placement, open craniotomies, endo-nasal/skull-based/ENT, and spine procedures.

Figure 11A:
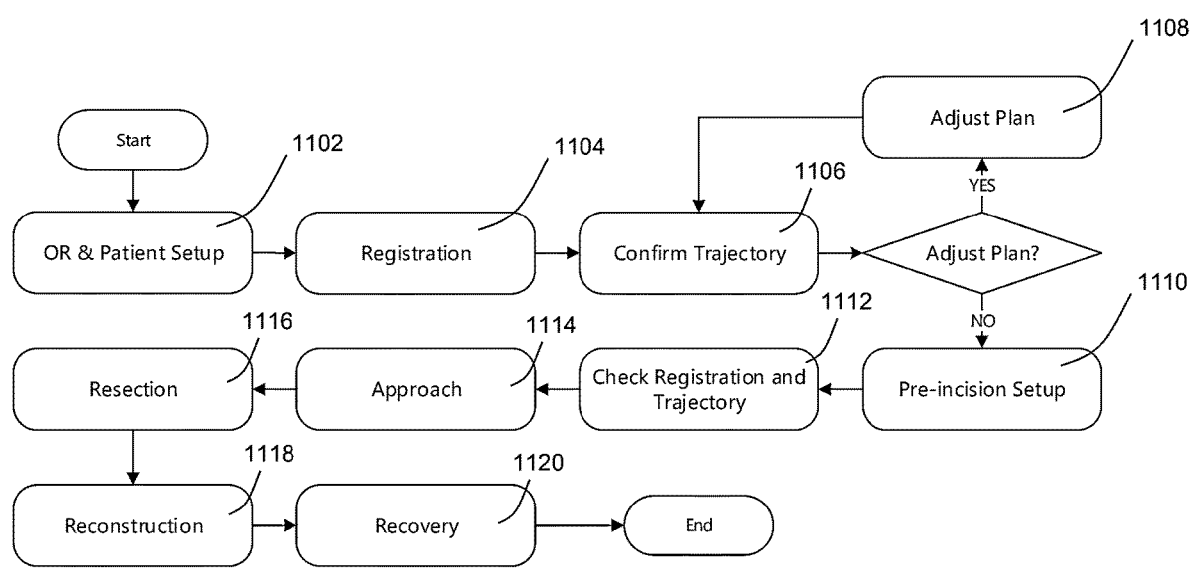
FIG. 11A is a flow chart illustrating alternate processing steps involved in a port based surgical procedure using a navigation system, in accordance with an embodiment of the present disclosure.

Referring to FIG. 11A, this flow chart illustrates alternative processing steps involved in a port-based surgical procedure using a navigation system, in accordance with an embodiment of the present disclosure. The process initiates with operating room (OR) and patient setup (step 1102). In step 1102, necessary equipment such as lights, the navigation system and surgical tools are set up. The patient is then prepped and pinned in the headrest. The next step is registration (step 1104) where the pose of the patient's head is determined relative to a base reference frame and the location of the base reference frame is correlated/registered to the imaging frame of reference.

Still referring to FIG. 11A, the next step is to confirm the trajectory (step 1106) where the port is positioned at the engagement point and the trajectory is displayed on the navigation system. The surgeon confirms that all equipment has sufficient line of sight and reach for the procedure. The surgeon then adjusts the plan (step 1108) where the surgeon creates a new engagement point and/or target point for surgery based on constraints observed in the operating room. The next step involves pre-incision setup (step 1110) where the patient and equipment are draped and the surgical site on the patient is shaved and sterilized. Thereafter, the registration and trajectory path are checked (step 1112) to ensure that the equipment, navigation system and plan are accurate.

Still referring to FIG. 11A, the next step in the procedure in FIG. 11A is the approach (step 1114) where a burr-hole craniotomy is created. A range of motion is tested with the port and intraoperative adjustment to trajectory is created if required. The dural opening is created and dural flap is stitched back. The port is then inserted down the trajectory via navigation guidance. Further a surgical camera is also positioned coaxially with the port.

Still referring to FIG. 11A, immediately after the approach (step 1114) is the resection step (step (1116) where the tumor is removed using a surgical tool such as the NICO MYRIAD® tool. The port may be moved around within the constraints of the craniotomy by the surgeon during the procedure to cover all extents of the tumor or ICH. The surgical camera is re-positioned as required for viewing down ports. Further any bleeding is cauterized as required.

Still referring to FIG. 11A, the next step involves reconstruction (step 1118) where the surgical site is irrigated via the port. The port is then slowly retracted while viewing surgical site via the surgical camera. A graft is glued on, the dura is stitched; and the bone flap is replaced. Finally, the head clamp is removed. The last and final step is recovery (step 1120) where the patent is sent to the recovery area in the hospital. If no hemorrhage occurs, the patient is sent home for recovery shortly after.

Still referring to FIG. 11A, a navigation system can also be used for a brain biopsy. Brain Biopsy is the insertion of a thin needle into a patient's brain for purposes of removing a sample of brain tissue. The brain tissue is subsequently assessed by a pathologist to determine if it is cancerous. Brain biopsy procedures can be conducted with or without a stereotactic frame. Both types of procedures are performed using image-guidance, but only frameless biopsies are conducted using a navigation system.

Figure 11B:
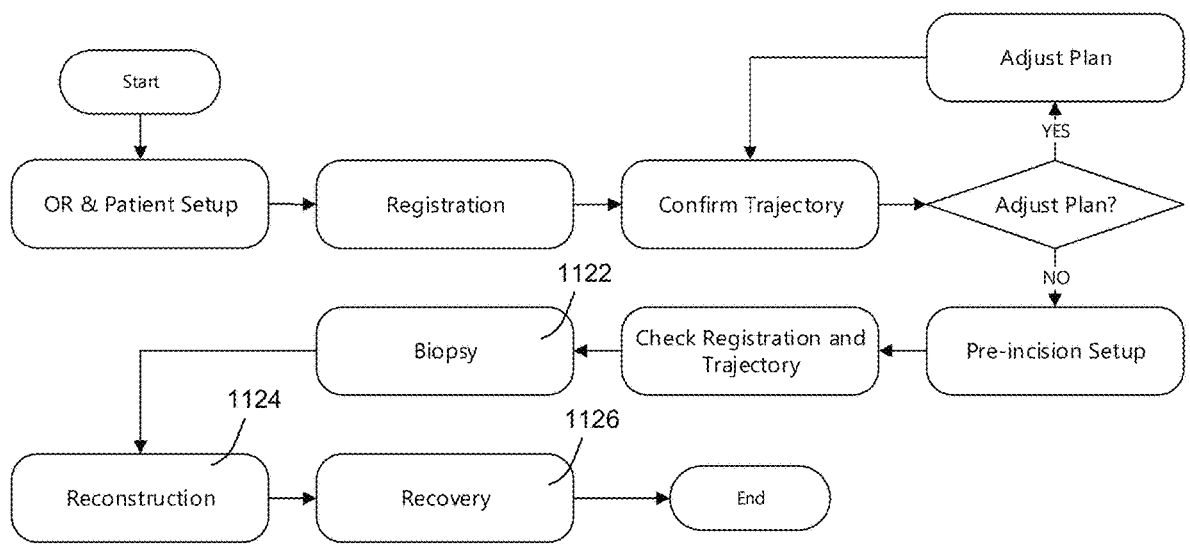
FIG. 11B is a flow chart illustrating processing steps involved in a brain biopsy surgical procedure using a navigation system, in accordance with an embodiment of the present disclosure.

Referring to FIG. 11B, this flow chart illustrates processing steps involved in a brain biopsy surgical procedure using a navigation system, in accordance with an embodiment of the present disclosure. The brain biopsy surgical procedure is very similar to a port-based surgical procedure (FIG. 11A) with the exception of the biopsy (step 1122), reconstruction (step 1124) and recovery steps (step 1126). In the biopsy step (step 1122), a small hole is drilled into the skull at the engagement point. The biopsy needle is guided through the hole, into the brain and to the planned target. The biopsy needle is tracked in real-time; and a biopsy sample is obtained and placed in a container for transportation to the pathology lab.

Still referring to FIG. 11B, the reconstruction (step 1124) and recovery steps (step 1126) are much shorter for the brain biopsy procedures since the opening is much smaller. As noted above, the biopsy needle is also tracked continuously by the navigation system. In further embodiment, the surgeon holds the biopsy needle, free hand, during the procedure. In other systems, a needle guide could be adhered to the skull, then positioned and oriented using the navigation system. If a depth-stop is included in this needle guide, the biopsy needle does not require continuous navigation.

Still referring to FIG. 11B, deep-brain stimulation (DBS) procedures implant a small electrode into a specific area of the brain for reduction of tremors from Parkinson's disease and dystonia. The electrode is connected to a control device implanted elsewhere in the body, typically near the clavicle. DBS can be conducted via a stereotactic frame or frameless. A navigation system may be contemplated for use with a frameless deep-brain stimulation procedure.

Figure 11C:
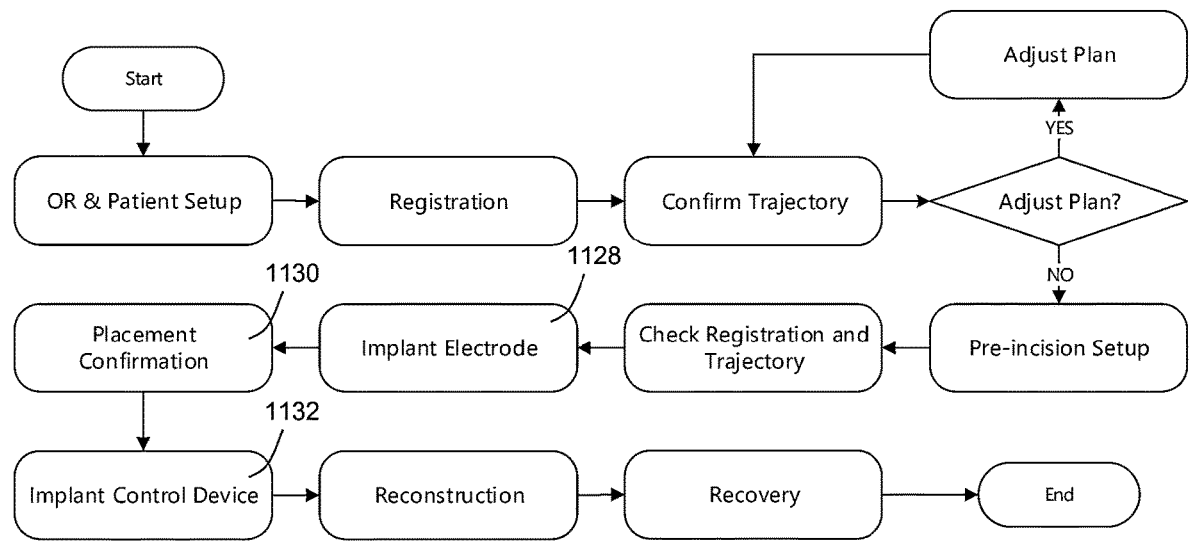
FIG. 11C is a flow chart illustrating the processing steps involved in a deep-brain stimulation procedure using a navigation system, in accordance with an embodiment of the present disclosure.

Referring to FIG. 11C, this flow chart illustrates the processing steps involved in a deep-brain stimulation procedure using a navigation system, in accordance with an embodiment of the present disclosure. The workflow for deep-brain stimulation outlined in FIG. 11C is similar to the brain biopsy procedure outline in FIG. 11B with the differences of the latter steps of implanting electrode (step 1128), placement confirmation (step 1130) and implanting a control device (step 1132).

Still referring to FIG. 11C, during the implant electrode step (step 1128), a small hole is drilled into the skull at the engagement point. A guidance device is positioned and oriented on the skull via the navigation system. An electrode lead is guided through the guidance device, into the brain and to the planned target. The electrode is also tracked in real-time with the navigation system. Thereafter, the workflow advances to the placement confirmation step (step 1130) where confirmation of electrode placement is obtained by either listening to activity on the electrode, and/or by test stimulation of the area via the electrode and observing patient response.

Still referring to FIG. 11C, after the placement confirmation step (step 1130), the workflow proceeds to the implant control device step (step 1132) where an incision is made in the location near the clavicle. A control device is inserted under the skin and attached to the clavicle. Electrodes leads are then routed under the skin from the electrode incision site to the control device. Thereafter, the process advances to the reconstruction (step 1118) and recovery (step 1120) steps as outlined in FIG. 11A.

Still referring to FIG. 11C, a catheter or a shunt placement may also be assisted by a navigation system. Shunts or catheters are inserted into the brain cavity to treat patients with hydrocephalus. Cranial pressure is too great in these patients as a result of excessive cerebral spinal fluid (CSF). A shunt or catheter is introduced under image guidance and the excess CSF is drained into another part of the body where it will be reabsorbed.

Figure 11D:
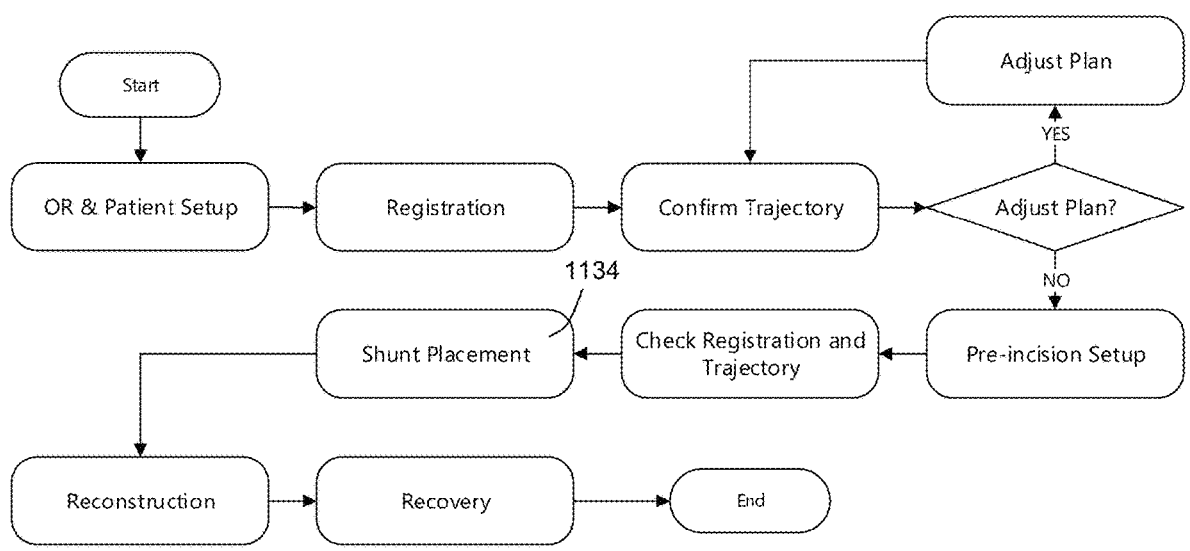
FIG. 11D a flow chart illustrating the processing steps involved in a catheter/shunt placement procedure using a navigation system, in accordance with an embodiment of the present disclosure.

Referring to FIG. 11D, this flow chart illustrates the processing steps involved in a catheter/shunt placement procedure using a navigation system, in accordance with an embodiment of the present disclosure. This procedure is similar to the brain biopsy procedure, as shown in FIG. 11B, with the replacement of the biopsy step (step 1122) with a shunt placement step (step 1134). In a shunt placement step (step 1134), a small hole is drilled into the skull at the engagement point. A guidance device is positioned and oriented on the skull via the navigation system. The shunt or catheter is guided through the guidance device, into the brain and to the planned target. The shunt or catheter is also tracked in real-time by the navigation system.

Update of Intraoperative Data

Still referring to FIG. 11D, an example embodiment of the navigation system may update preoperative images (for example rendered 3D MRI image data) with intraoperatively acquired localized MRI images, using an MRI imaging probe (for example as described in copending US Patent Publication US20160022146, which claims priority from U.S. Provisional Patent Application Ser. No. 61/801,746 filed on Mar. 15, 2013 entitled INSERTABLE IMAGING DEVICES AND METHODS OF USE THEREOF), which is incorporated herein in its entirety by reference. This can be accomplished by tracking the probe's location, e.g., spatial position and pose, relative to an anatomical part of a patient (this would be the brain for port-based surgery) which has been registered with its corresponding 3D preoperative MRI. Once the probe is in vicinity to image the anatomical part (such as a patient's brain) the probe actuates the MR scan. After the image is acquired the spatial position and pose of the imaging probe relative to the anatomical part, as determined by the tracking system, can be used to identify the location of the volume of the scan within the preoperative 3D image. The intraoperative image can then be registered with the preoperative image. Further low-resolution or low-quality portions of the preoperative image may be replaced by the localized intraoperative images.

Still referring to FIG. 11D, in one embodiment, during a port-base procedure, brain displacement or deformation can be predicted with accurate simulation, using a priori tissue stiffness information, geometric knowledge of the introducer and port, a biomechanical model of tissue deformation, (using the skull as a boundary condition) and using preoperative imaging data. This model is updated using real-time imaging information as the introducer is positioned inside of the head, and more accurately if real-time imaging is performed using the in-situ port. For instance, real-time ultrasound imaging done on the tip of the port, can detect tissue stiffness inside the brain. This information is used instead of the a priori predicted stiffness and can provide a better estimate of tissue movement. In addition, ultrasound can be used to identify sulci patterns as the port is being introduced. These sulci patterns are matched to the preoperative sulcus patterns, and a deformed preoperative model can be generated based on this information.

Still referring to FIG. 11D, in this iterative manner, the model will be updated by the system according to information obtained during the procedure to provide for accurate representations of the tumor location, for instance, modeling of tumor roll within the brain, and also the ability to measure the total stress and strain on nerve fibers as the port is inserted into the brain. This is represented by the system as a global value and as with the weighting of the hierarchy of the fibers, the actual strain of the fibers may be used to calculate a value associated with the invasiveness of a surgical approach.

Still referring to FIG. 11D, there may be a discrepancy between the preoperative imaging data, and the real-time port information (US, OCT, photo acoustic, and optical). This is measured by matching sulcal patterns, blood vessel positions, or by quantifiable common contrast mechanisms such as elastic modulus, tissue anisotropy, blood-flow, etc. The real-time port information is expected to represent the truth, and when there is a significant discrepancy, a scan would be done to update the volumetric MRI and/or CT scans to update the preoperative, or intraoperative, scanning volume. In the optimal configuration, an MRI port coil is used in conjunction with an external MRI system to acquire a 3D volume demonstrating sulci path, tumor, nerve fascicles by way of DTI acquisition, and blood vessels. As the acquisition time is typically much longer than US, OCT or photo-acoustic imaging, it is not expected to be used as a real-time modality, however it can be effectively utilized as a single modality to position the access port with pseudo-real time capability (typically not faster than 1 fps). Future availability of faster acquisition technologies may provide a near real-time DTI information using a port coil.

While the Applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

What is claimed:

1. A method of supporting a medical procedure by way of a control and processing unit, the method comprising:
    providing the control and processing unit, comprising:
        providing a navigation module, providing the navigation module comprising providing a navigation system and configuring the navigation module to control trajectory and visual display of at least one medical instrument, providing the navigation module comprising providing a power supply, providing a processor control module programmed with navigation control software, and providing a storage device connected to the processor control module, providing the storage device comprising storing, therein, a surgical trajectory path plan defining a surgical path to be followed on an anatomical part undergoing a medical procedure, and the at least one medical instrument comprising at least one uniquely identifiable tracking marker associated therewith, and providing the storage device comprising configuring the storage device to store: a virtual representation of the at least one medical instrument stored in the storage device with the at least one associated uniquely identifiable tracking marker, the virtual representation of the at least one medical instrument being geometrically accurate with respect to volume, size, and shape of the at least one medical instrument; and a virtual representation of at least one tissue structure of interest of the anatomical part from the surgical trajectory path plan stored in the storage device;
    providing a tracking system in communication with the navigation system which determines spatial positioning of the at least one medical instrument using the at least one associated uniquely identifiable tracking marker, providing the tracking system comprising providing a 3D optical tracking stereo camera,
    providing the processor control module comprising programming the processor control module with instructions to: compare the at least one medical instrument, being tracked, with the geometrically accurate virtual representation of the at least one medical instrument stored in the storage device for identifying the at least one medical instrument in use, adaptively update a section of a preoperative image by using a localized intraoperative image, the preoperative imaging data acquired using MRI, calculate a course change from an actual surgical path back to the surgical path defined by the surgical trajectory path plan, and match the virtual representation of the at least one tissue structure with an actual view of the at least one tissue structure of interest;
    providing at least one display for displaying a superposition of a virtual representation of the surgical path defined by the surgical trajectory path plan and a virtual representation of the actual surgical path, preoperative imaging data of the anatomical part undergoing the medical procedure which is registered with the anatomical part, an image of the at least one medical instrument used in the medical procedure, the virtual representation of at least one tissue structure from the surgical trajectory path plan, the matched virtual representation of the at least one tissue structure with the actual view of the at least one tissue structure of interest, the course change from the virtual representation of the actual surgical path back to the virtual representation of the surgical path defined by the surgical trajectory path plan, the preoperative imaging data comprising diffusion tensor imaging data, the diffusion tensor imaging data comprising at least four dimensions of information, and the at least four dimensions of information comprising three spatial dimensions and a time dimension,
    providing the navigation system comprising providing a guidance mechanism for visually assisting a surgeon to translate one medical instrument of the at least one medical instrument, being tracked by the tracking system, along the surgical path, and
    providing the navigation module comprising programming the navigation module to use the intraoperative imaging data of a localized region for updating the preoperative imaging data of the localized region within the anatomical part to update imaging of intraoperative tissue structures; and
    providing at least one imaging device configured to acquire intraoperative imaging data of a localized region within the anatomical part during the medical procedure, the at least one imaging device comprising at least one uniquely identifiable tracking marker associated therewith which is tracked by the tracking system, wherein the navigation module updates the preoperative imaging data of the localized region within the anatomical part during the medical procedure based on positional information of the tracked imaging device relative to the anatomical part, providing the at least one imaging device comprising providing at least one MRI device insertable into the anatomical part, and providing the navigation module comprising programming the navigation module to adaptively update a section of the preoperative imaging data using localized intraoperative MRI imaging data acquired using the at least one MRI device insertable into the anatomical part, whereby real-time feedback is providable, the real-time feedback comprising at least one spatially correlated color map corresponding to at least one spectral signature from acquired intraoperative information; and operating the control and processing unit.

2. The method of claim 1, wherein providing the navigation module comprises programming the navigation module to provide positionally accurate maps correlating intraoperative imaging data acquired during the medical procedure to locations where the intraoperative imaging data is acquired in the anatomical part.

3. The method of claim 2, wherein providing the navigation module comprises programming the navigation module to represent the positionally accurate maps by spatially correlated color maps.

4. The method of claim 1, wherein providing the navigation module comprises programming the navigation module to enable quantitative registration in which an absolute quantitative metric is measured intraoperatively and to use the absolute quantitative metric to register imaging data obtained using one or more imaging modalities.

5. The method of claim 4, wherein providing the navigation module comprises programming the navigation module to enable quantitative registration in which an absolute quantitative comprises at least one of: MRI (T1), MRI (T2), cell density, tissue density, tissue anisotropy, tissue stiffness, fluid flow per volume or area, electrical conductivity, pH, and pressure.

6. The method of claim 1, wherein providing the navigation module comprises programming the navigation module to compute biomechanical properties of tissue being imaged by the at least one imaging device and to use the computed biomechanical properties to update a tissue model of the anatomical part undergoing the medical procedure.

7. The method of claim 1, wherein providing the navigation module comprises programming the navigation module to analyze tissue patterns from the intraoperative imaging data acquired by the at least one imaging device and to compare the tissue patterns from the intraoperative imaging data acquired by the at least one imaging device with the preoperative imaging data, whereby a comparison is providable, and, based on the comparison, to generate a deformed preoperative model of the anatomical part.

8. The method of claim 1, wherein providing the at least one imaging device comprises providing at least one of: an ultrasound imaging device, an optical coherence tomography imaging device, a photo acoustic imaging device, and an optical imaging device.

9. The method of claim 1, wherein providing the at least one imaging device comprises configuring the at least one imaging device to image tissue structures, and wherein providing the navigation module comprises configuring the navigation module to use the intraoperative imaging data of imaged tissue structures to update the preoperative imaging data of the tissue structures.

10. The method of claim 1, wherein providing a navigation module, the anatomical part comprises a patient's brain, the medical procedure comprises a port-based surgery utilizing a port and introducer, and wherein the surgical path comprises a multi-segment surgical path defined by a multi-segment surgical trajectory path plan.

11. The method of claim 10, wherein providing the at least one imaging device comprises configuring the at least one imaging device to image at least one tissue structure of the brain comprising at least one of: brain fiber tracts, sulci structures, nerve fascicles, and blood vessels.

12. The method of claim 1, wherein providing the navigation module comprises programming the navigation module to:
compare the preoperative imaging data and the intraoperative imaging data;
detect discrepancies between the preoperative imaging data and the intraoperative imaging data; and
upon detecting discrepancies, perform a scan to update at least one of volumetric scans and CT scans,
whereby at least one of preoperative scanning volumes and intraoperative scanning volumes are updateable.

13. The method of claim 12, wherein providing the navigation module comprises programming the navigation module to compare and detect discrepancies between the preoperative imaging data and the intraoperative imaging data by matching at least one of sulcal patterns, blood vessel positions, and, by quantifiable common contrast mechanisms, elastic modulus, tissue anisotropy, and blood-flow.

14. The method of claim 1, wherein providing the navigation module comprises programming the navigation module to visually display preoperative imaging data, intraoperative imaging data, a superposition of the preoperative and intraoperative imaging data, the virtual representation of the surgical path defined by the surgical trajectory path plan in both the preoperative and intraoperative imaging data, and a virtual representation of an actual surgical path calculated by the navigation module based on the intraoperative imaging data.

15. The method of claim 14, wherein providing the processor control module comprises configuring the processor control module to calculate course change from the actual surgical path back to the surgical path defined by the surgical trajectory path plan is consistent with surgical outcome criteria associated with the surgical trajectory path plan with respect to regions of the anatomical part to be avoided or approached, and wherein providing the at least one display comprise configuring the at least one display device to display a course change from the actual surgical path back to the surgical path defined by the surgical trajectory path plan is consistent with surgical outcome criteria associated with the surgical trajectory path plan with respect to regions of the anatomical part to be avoided or approached.

16. The method of claim 1, wherein the at least one tissue structure from the surgical trajectory path plan comprises at least one of: fiber tracts, sulci structures, nerve fascicles, and blood vessels.

17. A method of supporting a medical procedure on a patient by way of a control and processing unit, comprising:
providing the control and processing unit, comprising:
providing a navigation module, providing the navigation module comprising providing a navigation system and configuring the navigation module to control trajectory and visual display of at least one medical instrument, providing the navigation module comprising: providing a power supply, providing a processor control module programmed with navigation control software, and providing a storage device connected to the processor control module, providing the storage device comprising storing, therein, a surgical trajectory path plan defining a surgical path to be followed on an anatomical part undergoing the medical procedure and preoperative imaging data of the anatomical part of the patient undergoing the medical procedure, each at least one medical instrument comprising at least one uniquely identifiable tracking marker associated therewith, and providing the storage device comprising configuring the storage device to store: a virtual representation of the at least one medical instrument with its associated at least one uniquely identifiable tracking marker, the virtual representation of the at least one medical instrument being geometrically accurate with respect to size and shape of the at least one medical instrument, and a virtual representation of at least one tissue structure from the surgical trajectory path plan stored in the storage device;

providing a 3D tracking stereo camera in communication with the navigation system for determining spatial positioning of the at least one medical instrument using the at least one uniquely identifiable tracking marker and associated virtual representation relative to the registered anatomical part, the tracking camera comprising a 3D optical tracking stereo camera;

providing the processor control module comprising programming the processor control module to compare at least one medical instrument, being tracked, with the geometrically accurate virtual representation of the at least one medical instrument stored in the storage device for: identifying the at least one medical instrument in use, adaptively update a section of a preoperative image by using a localized intraoperative image, calculate a course change from an actual surgical path back to the surgical path defined by the surgical trajectory path plan, and match the virtual representation of the at least one tissue structure with an actual view of at least one tissue structure of interest;

providing at least one display for displaying: a superposition of a virtual representation of the surgical path defined by the surgical plan and a virtual representation of the actual surgical path, the preoperative imaging data of the anatomical part undergoing the medical procedure which is registered with the anatomical part, an image of the at least one medical instrument used in the medical procedure, the virtual representation of at least one tissue structure from the surgical trajectory path plan, the matched virtual representation of the at least one tissue structure with the actual view of the at least one tissue structure of interest, the course change from the virtual representation of the actual surgical path back to the virtual representation of the surgical path defined by the surgical trajectory path plan, the preoperative imaging data comprising diffusion tensor imaging data, the diffusion tensor imaging data comprising at least four dimensions of information, and the at least four dimensions of information comprising three spatial dimensions and a time dimension;

providing an imaging device providing the imaging device comprising configuring the imaging device to acquire intraoperative imaging data of a localized region within the anatomical part, the imaging device comprising at least one uniquely identifiable tracking marker associated therewith tracked by the tracking camera; and the navigation module programmed with instructions to use the intraoperative imaging data of the localized region for updating the preoperative imaging data of the localized region within the anatomical part during the medical procedure based on positional information of the tracked imaging device relative to the anatomical part, whereby real-time feedback is providable, the real-time feedback comprising at least one spatially correlated color map corresponding to at least one spectral signature from acquired intraoperative information, wherein the preoperative imaging data are acquired using MRI, wherein the imaging device is an insertable MRI device inserted into the anatomical part, and wherein the navigation module is programmed to adaptively update a section of the MRI acquired preoperative imaging data using localized intraoperative MRI imaging data acquired using the insertable MRI device; and operating the control and processing unit.

18. The method of claim 17, wherein operating the control and processing unit comprises:

using the navigation module, controlling the trajectory and the visual display of the at least one medical instrument;

determining the spatial positioning of the at least one medical instrument using the at least one associated uniquely identifiable tracking marker;

using the at least one display, displaying the superposition of the virtual representation of the surgical path defined by the surgical trajectory path plan and the virtual representation of the actual surgical path;

using the at least one display, visually assisting translating one medical instrument of the at least one medical instrument, being tracked by the tracking system, along the surgical path;

updating the preoperative imaging data of the localized region within the anatomical part for updating imaging of intraoperative tissue structures by using the intraoperative imaging data of a localized region;

acquiring the intraoperative imaging data of the localized region within the anatomical part during the medical procedure; and adaptively updating the section of the preoperative imaging data by using localized intraoperative MRI imaging data acquired, thereby providing the real-time feedback.

19. The method of claim 18, wherein providing the navigation module comprises programming the navigation module to provide positionally accurate maps correlating intraoperative imaging data, acquired during the medical procedure, to locations where the intraoperative imaging data is acquired in the anatomical part.

20. The method of claim 19, wherein programming the processor control module comprises configuring the processor to match the virtual representation of the at least one tissue structure, from the surgical trajectory path plan, comprising at least one of fiber tracts, sulci structures, nerve fascicles, and blood vessels, with an actual view of the at least one tissue structure of interest.

\* \* \* \* \*